US008246678B2

(12) United States Patent
Salahieh et al.

(10) Patent No.: US 8,246,678 B2
(45) Date of Patent: Aug. 21, 2012

(54) METHODS AND APPARATUS FOR ENDOVASCULARLY REPLACING A PATIENT'S HEART VALVE

(75) Inventors: Amr Salahieh, Saratoga, CA (US);
Ulrich R. Haug, Campbell, CA (US);
Hans F. Valencia, Berkeley, CA (US);
Robert A. Geshlider, San Francisco, CA (US); Tom Saul, El Granada, CA (US);
Dwight P. Morejohn, Davis, CA (US)

(73) Assignee: Sadra Medicl, Inc., Los Gatos, CA (US)

( * ) Notice: Subject to any disclaimer, the term of this patent is extended or adjusted under 35 U.S.C. 154(b) by 1041 days.

(21) Appl. No.: 11/716,123

(22) Filed: Mar. 9, 2007

(65) Prior Publication Data

US 2007/0162107 A1   Jul. 12, 2007

Related U.S. Application Data

(63) Continuation of application No. 10/893,151, filed on Jul. 15, 2004, now abandoned, which is a continuation-in-part of application No. 10/746,280, filed on Dec. 23, 2003.

(51) Int. Cl.
 *A61F 2/24* (2006.01)
(52) U.S. Cl. ..................................... 623/2.11
(58) Field of Classification Search ........... 623/2.1–2.19
 See application file for complete search history.

(56) References Cited

U.S. PATENT DOCUMENTS

| 15,192 A | 6/1856 | Peale |
|---|---|---|
| 2,682,057 A | 6/1954 | Lord |
| 2,701,559 A | 2/1955 | Cooper |
| 2,832,078 A | 4/1958 | Williams |
| 3,099,016 A | 7/1963 | Edwards |
| 3,113,586 A | 12/1963 | Edmark, Jr. |
| 3,130,418 A | 4/1964 | Head et al. |
| 3,143,742 A | 8/1964 | Cromie |
| 3,221,006 A | 11/1965 | Moore et al. |
| 3,334,629 A | 8/1967 | Cohn |
| 3,367,364 A | 2/1968 | Cruz, Jr. et al. |
| 3,409,013 A | 11/1968 | Berry |
| 3,445,916 A | 5/1969 | Schulte |
| 3,540,431 A | 11/1970 | Mobin-Uddin |

(Continued)

FOREIGN PATENT DOCUMENTS

CN    1338951 A    3/2002

(Continued)

OTHER PUBLICATIONS

Salahieh, et al., U.S. Appl. No. 12/264,082 entitled "Repositionable heart valve and method," filed Nov. 3, 2008.

(Continued)

*Primary Examiner* — William H. Matthews
(74) *Attorney, Agent, or Firm* — Vidas, Arrett & Steinkraus, P.A.

(57) ABSTRACT

The present invention provides methods and apparatus for endovascularly replacing a patient's heart valve. The apparatus includes a replacement valve and an anchor having an expandable braid. In some embodiments, the expandable braid is fabricated from a single strand of wire. In some embodiments, the expandable braid comprises at least one turn feature. The anchor and the valve preferably are configured for endovascular delivery and deployment.

12 Claims, 23 Drawing Sheets

U.S. PATENT DOCUMENTS

| | | |
|---|---|---|
| 3,548,417 A | 12/1970 | Kischer |
| 3,570,014 A | 3/1971 | Hancock |
| 3,587,115 A | 6/1971 | Shiley |
| 3,592,184 A | 7/1971 | Watkins |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,997,923 A | 12/1976 | Possis |
| 4,035,849 A | 7/1977 | Angell et al. |
| 4,056,854 A | 11/1977 | Boretos et al. |
| 4,106,126 A | 8/1978 | Traenkle |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos et al. |
| 4,291,420 A | 9/1981 | Reul |
| 4,297,749 A | 11/1981 | Davis et al. |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,423,809 A | 1/1984 | Mazzocco |
| 4,425,908 A | 1/1984 | Simon |
| 4,470,157 A | 9/1984 | Love |
| 4,484,579 A | 11/1984 | Meno et al. |
| 4,501,030 A | 2/1985 | Lane |
| 4,531,943 A | 7/1985 | Van Tassel |
| 4,535,483 A | 8/1985 | Klawitter et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,680,031 A | 7/1987 | Alonso |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,829,990 A | 5/1989 | Thüroff et al. |
| 4,834,755 A | 5/1989 | Silvestrini et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,064,435 A | 11/1991 | Porter |
| 5,080,668 A | 1/1992 | Bolz et al. |
| 5,085,635 A | 2/1992 | Cragg |
| 5,089,015 A | 2/1992 | Ross |
| 5,132,473 A | 7/1992 | Furutaka et al. |
| 5,141,494 A | 8/1992 | Danforth et al. |
| 5,143,987 A | 9/1992 | Hansel et al. |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,167,628 A | 12/1992 | Boyles |
| 5,209,741 A | 5/1993 | Spaeth |
| 5,215,541 A | 6/1993 | Nashef et al. |
| 5,217,481 A | 6/1993 | Barbara |
| 5,217,483 A | 6/1993 | Tower |
| 5,258,042 A | 11/1993 | Mehta |
| 5,282,847 A | 2/1994 | Trescony et al. |
| 5,295,958 A | 3/1994 | Shturman |
| 5,332,402 A | 7/1994 | Teitelbaum |
| 5,336,258 A | 8/1994 | Quintero et al. |
| 5,350,398 A | 9/1994 | Pavcnik et al. |
| 5,360,444 A | 11/1994 | Kusuhara |
| 5,370,685 A | 12/1994 | Stevens |
| 5,389,106 A | 2/1995 | Tower |
| 5,397,351 A | 3/1995 | Pavcnik et al. |
| 5,409,019 A | 4/1995 | Wilk |
| 5,411,552 A | 5/1995 | Andersen et al. |
| 5,425,762 A | 6/1995 | Muller |
| 5,431,676 A | 7/1995 | Dubrul et al. |
| 5,443,446 A | 8/1995 | Shturman |
| 5,443,449 A | 8/1995 | Buelna |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,480,424 A | 1/1996 | Cox |
| 5,500,014 A | 3/1996 | Quijano et al. |
| 5,507,767 A | 4/1996 | Maeda et al. |
| 5,534,007 A | 7/1996 | St. Germain et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,571,175 A | 11/1996 | Vanney et al. |
| 5,571,215 A | 11/1996 | Sterman et al. |
| 5,573,520 A | 11/1996 | Schwartz |
| 5,575,818 A | 11/1996 | Pinchuk |
| 5,591,185 A | 1/1997 | Kilmer et al. |
| 5,591,195 A | 1/1997 | Taheri et al. |
| 5,607,464 A | 3/1997 | Trescony et al. |
| 5,609,626 A | 3/1997 | Quijano et al. |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,693,310 A | 12/1997 | Gries et al. |
| 5,695,498 A | 12/1997 | Tower |
| 5,709,713 A | 1/1998 | Evans |
| 5,713,951 A | 2/1998 | Garrison |

| | | |
|---|---|---|
| 5,713,953 A | 2/1998 | Vallana et al. |
| 5,716,370 A | 2/1998 | Williamson, IV et al. |
| 5,716,417 A | 2/1998 | Girard et al. |
| 5,720,391 A | 2/1998 | Dohm et al. |
| 5,728,068 A | 3/1998 | Leone et al. |
| 5,733,325 A | 3/1998 | Robinson et al. |
| 5,735,842 A | 4/1998 | Krueger et al. |
| 5,749,890 A | 5/1998 | Shaknovich |
| 5,756,476 A | 5/1998 | Epstein et al. |
| 5,769,812 A | 6/1998 | Stevens et al. |
| 5,800,456 A | 9/1998 | Maeda et al. |
| 5,800,531 A | 9/1998 | Cosgrove et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,840,081 A | 11/1998 | Andersen et al. |
| 5,843,158 A | 12/1998 | Lenker et al. |
| 5,855,597 A | 1/1999 | Jayaraman |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,868,783 A | 2/1999 | Tower |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,906,619 A | 5/1999 | Olson et al. |
| 5,907,893 A | 6/1999 | Zadno-Azizi et al. |
| 5,910,154 A | 6/1999 | Tsugita et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,968,070 A | 10/1999 | Bley et al. |
| 5,984,957 A | 11/1999 | Laptewicz, Jr. et al. |
| 5,984,959 A | 11/1999 | Robertson et al. |
| 5,993,469 A | 11/1999 | McKenzie et al. |
| 5,997,557 A | 12/1999 | Barbut et al. |
| 6,010,522 A | 1/2000 | Barbut et al. |
| 6,022,370 A | 2/2000 | Tower |
| 6,027,520 A | 2/2000 | Tsugita et al. |
| 6,027,525 A | 2/2000 | Suh et al. |
| 6,042,598 A | 3/2000 | Tsugita et al. |
| 6,042,607 A | 3/2000 | Williamson, IV et al. |
| 6,051,014 A | 4/2000 | Jang |
| 6,051,104 A | 4/2000 | Oriaran et al. |
| 6,059,827 A | 5/2000 | Fenton |
| 6,074,418 A | 6/2000 | Buchanan |
| 6,093,203 A | 7/2000 | Uflacker |
| 6,096,074 A | 8/2000 | Pedros |
| 6,123,723 A | 9/2000 | Konya et al. |
| 6,132,473 A | 10/2000 | Williams et al. |
| 6,142,987 A | 11/2000 | Tsugita |
| 6,143,987 A | 11/2000 | Makita |
| 6,146,366 A | 11/2000 | Schachar |
| 6,162,245 A | 12/2000 | Jayaraman |
| 6,165,200 A | 12/2000 | Tsugita et al. |
| 6,165,209 A | 12/2000 | Patterson et al. |
| 6,168,579 B1 | 1/2001 | Tsugita |
| 6,168,614 B1 | 1/2001 | Andersen et al. |
| 6,171,327 B1 | 1/2001 | Daniel et al. |
| 6,171,335 B1 | 1/2001 | Wheatley et al. |
| 6,179,859 B1 | 1/2001 | Bates |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,214,036 B1 | 4/2001 | Letendre et al. |
| 6,221,006 B1 | 4/2001 | Dubrul et al. |
| 6,221,091 B1 | 4/2001 | Khosravi |
| 6,221,096 B1 | 4/2001 | Aiba et al. |
| 6,221,100 B1 | 4/2001 | Strecker |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 * | 6/2001 | Stinson et al. ............... 623/1.34 |
| 6,258,114 B1 | 7/2001 | Konya et al. |
| 6,258,115 B1 | 7/2001 | Dubrul |
| 6,258,120 B1 | 7/2001 | McKenzie et al. |
| 6,267,783 B1 | 7/2001 | Letendre et al. |
| 6,270,513 B1 | 8/2001 | Tsugita et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,417 B1 | 10/2001 | Spence et al. |
| 6,319,281 B1 | 11/2001 | Patel |
| 6,327,772 B1 | 12/2001 | Zadno-Azizi et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,346,116 B1 | 2/2002 | Brooks et al. |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,364,895 B1 | 4/2002 | Greenhalgh |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,416,510 B1 | 7/2002 | Altman et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,660 B2 | 10/2002 | Ogle et al. |
| 6,475,239 B1 | 11/2002 | Campbell et al. |
| 6,482,228 B1 | 11/2002 | Norred |
| 6,485,501 B1 | 11/2002 | Green |
| 6,485,502 B2 | 11/2002 | Don Michael et al. |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,537,297 B2 | 3/2003 | Tsuigita et al. |
| 6,540,768 B1 | 4/2003 | Diaz et al. |
| 6,562,058 B2 | 5/2003 | Seguin et al. |
| 6,569,196 B1 | 5/2003 | Vesely |
| 6,592,546 B1 | 7/2003 | Barbut et al. |
| 6,592,614 B2 | 7/2003 | Lenker et al. |
| 6,605,112 B1 | 8/2003 | Moll et al. |
| 6,610,077 B1 | 8/2003 | Hancock et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,632,243 B1 | 10/2003 | Zadno-Azizi et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,652,578 B2 | 11/2003 | Bailey et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin, Jr. et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |

| | | | |
|---|---|---|---|
| 6,689,164 B1 | 2/2004 | Seguin | |
| 6,692,512 B2 | 2/2004 | Jang | |
| 6,695,864 B2 | 2/2004 | Macoviak et al. | |
| 6,695,865 B2 | 2/2004 | Boyle et al. | |
| 6,702,851 B1 | 3/2004 | Chinn et al. | |
| 6,712,842 B1 | 3/2004 | Gifford et al. | |
| 6,712,843 B2 | 3/2004 | Elliott | |
| 6,714,842 B1 | 3/2004 | Ito | |
| 6,719,789 B2 | 4/2004 | Cox | |
| 6,723,116 B2 | 4/2004 | Taheri | |
| 6,730,118 B2 | 5/2004 | Spenser et al. | |
| 6,730,377 B2 | 5/2004 | Wang | |
| 6,733,525 B2 | 5/2004 | Yang et al. | |
| 6,736,846 B2 | 5/2004 | Cox | |
| 6,752,828 B2 | 6/2004 | Thornton | |
| 6,758,855 B2 | 7/2004 | Fulton, III et al. | |
| 6,764,503 B1 | 7/2004 | Ishimaru | |
| 6,764,509 B2 | 7/2004 | Chinn et al. | |
| 6,767,345 B2 | 7/2004 | St. Germain et al. | |
| 6,769,434 B2 | 8/2004 | Liddicoat et al. | |
| 6,773,454 B2 | 8/2004 | Wholey et al. | |
| 6,776,791 B1 | 8/2004 | Stallings et al. | |
| 6,786,925 B1 | 9/2004 | Schoon et al. | |
| 6,790,229 B1 | 9/2004 | Berreklouw | |
| 6,790,230 B2 | 9/2004 | Beyersdorf et al. | |
| 6,790,237 B2 | 9/2004 | Stinson | |
| 6,792,979 B2 | 9/2004 | Konya et al. | |
| 6,797,002 B2 | 9/2004 | Spence et al. | |
| 6,814,746 B2 | 11/2004 | Thompson et al. | |
| 6,821,297 B2 | 11/2004 | Snyders | |
| 6,824,041 B2 | 11/2004 | Grieder | |
| 6,830,585 B1 | 12/2004 | Artof et al. | |
| 6,837,901 B2 | 1/2005 | Rabkin et al. | |
| 6,840,957 B2 | 1/2005 | DiMatteo et al. | |
| 6,843,802 B1 | 1/2005 | Villalobos et al. | |
| 6,849,085 B2 | 2/2005 | Marton | |
| 6,863,668 B2 | 3/2005 | Gillespie et al. | |
| 6,863,688 B2 | 3/2005 | Ralph | |
| 6,866,650 B2 | 3/2005 | Stevens et al. | |
| 6,872,223 B2 | 3/2005 | Roberts et al. | |
| 6,872,226 B2 | 3/2005 | Cali et al. | |
| 6,875,231 B2 | 4/2005 | Anduiza et al. | |
| 6,881,220 B2 | 4/2005 | Edwin et al. | |
| 6,887,266 B2 | 5/2005 | Williams et al. | |
| 6,890,340 B2 | 5/2005 | Duane | |
| 6,893,459 B1 | 5/2005 | Macoviak | |
| 6,893,460 B2 | 5/2005 | Spenser et al. | |
| 6,905,743 B1 | 6/2005 | Chen et al. | |
| 6,908,481 B2 | 6/2005 | Cribier | |
| 6,911,036 B2 | 6/2005 | Douk et al. | |
| 6,911,043 B2 | 6/2005 | Myers et al. | |
| 6,936,058 B2 | 8/2005 | Forde et al. | |
| 6,936,067 B2 | 8/2005 | Buchanan | |
| 6,951,571 B1 | 10/2005 | Srivastava | |
| 6,953,332 B1 | 10/2005 | Kurk et al. | |
| 6,964,673 B2 | 11/2005 | Tsugita et al. | |
| 6,969,395 B2 | 11/2005 | Eskuri | |
| 6,972,025 B2 | 12/2005 | WasDyke | |
| 6,974,464 B2 | 12/2005 | Quijano et al. | |
| 6,974,474 B2 | 12/2005 | Pavcnik et al. | |
| 6,974,476 B2 | 12/2005 | McGuckin, Jr. et al. | |
| 6,979,350 B2 | 12/2005 | Moll et al. | |
| 6,984,242 B2 | 1/2006 | Campbell et al. | |
| 6,989,027 B2 | 1/2006 | Allen | |
| 7,011,681 B2 | 3/2006 | Veseley | |
| 7,018,406 B2 | 3/2006 | Seguin et al. | |
| 7,025,791 B2 | 4/2006 | Levine et al. | |
| 7,037,331 B2 | 5/2006 | Mitelberg et al. | |
| 7,041,132 B2 | 5/2006 | Quijano et al. | |
| 7,097,658 B2 | 8/2006 | Oktay | |
| 7,122,020 B2 | 10/2006 | Mogul | |
| 7,125,418 B2 | 10/2006 | Duran | |
| 7,166,097 B2 | 1/2007 | Barbut | |
| 7,175,653 B2 | 2/2007 | Gaber | |
| 7,175,654 B2 | 2/2007 | Bonsignore et al. | |
| 7,175,656 B2 | 2/2007 | Khairkhahan | |
| 7,189,258 B2 | 3/2007 | Johnson et al. | |
| 7,191,018 B2 | 3/2007 | Gielen et al. | |
| 7,201,772 B2 | 4/2007 | Schwammenthal et al. | |
| 7,235,093 B2 | 6/2007 | Gregorich | |
| 7,258,696 B2 | 8/2007 | Rabkin et al. | |
| 7,267,686 B2 | 9/2007 | DiMatteo | |
| 7,276,078 B2 | 10/2007 | Spenser et al. | |
| 7,322,932 B2 | 1/2008 | Xie | |
| 7,329,279 B2 | 2/2008 | Haug et al. | |
| 7,374,560 B2 | 5/2008 | Ressemann et al. | |
| 7,381,219 B2 | 6/2008 | Salahieh et al. | |
| 7,381,220 B2 | 6/2008 | Macoviak | |
| 7,399,315 B2 | 7/2008 | Iobbi | |
| 7,445,631 B2 | 11/2008 | Salahieh et al. | |
| 7,470,285 B2 | 12/2008 | Nugent | |
| 7,510,574 B2 | 3/2009 | Trong-Phi | |
| 7,524,330 B2 | 4/2009 | Berreklouw | |
| 7,530,995 B2 | 5/2009 | Quijano | |
| 7,544,206 B2 | 6/2009 | Cohn | |
| 7,622,276 B2 | 11/2009 | Cunanan et al. | |
| 7,628,803 B2 | 12/2009 | Pavcnik | |
| 7,632,298 B2 | 12/2009 | Hijlkema et al. | |
| 7,712,606 B2 | 5/2010 | Salahieh et al. | |
| 7,722,666 B2 | 5/2010 | Lafontaine | |
| 7,748,389 B2 | 7/2010 | Salahieh et al. | |
| 7,780,725 B2 | 8/2010 | Haug et al. | |
| 7,803,185 B2 | 9/2010 | Gabbay | |
| 7,833,262 B2 | 11/2010 | McGuckin | |
| 7,846,204 B2 | 12/2010 | Letac et al. | |
| 2001/0002445 A1 | 5/2001 | Vesely | |
| 2001/0007956 A1 | 7/2001 | Letac et al. | |
| 2001/0010017 A1 | 7/2001 | Letac et al. | |
| 2001/0021872 A1 | 9/2001 | Bailey et al. | |
| 2001/0025196 A1 | 9/2001 | Chinn et al. | |
| 2001/0032013 A1 | 10/2001 | Marton | |
| 2001/0039450 A1 | 11/2001 | Pavcnik et al. | |
| 2001/0041928 A1 | 11/2001 | Pavcnik et al. | |
| 2001/0041930 A1 | 11/2001 | Globerman et al. | |
| 2001/0044634 A1 | 11/2001 | Don Michael et al. | |
| 2001/0044652 A1 | 11/2001 | Moore | |
| 2001/0044656 A1 | 11/2001 | Williamson et al. | |
| 2002/0002396 A1 | 1/2002 | Fulkerson | |
| 2002/0010489 A1 | 1/2002 | Grayzel et al. | |
| 2002/0026233 A1 | 2/2002 | Shaknovich | |
| 2002/0029014 A1 | 3/2002 | Jayaraman | |
| 2002/0029981 A1 | 3/2002 | Nigam | |
| 2002/0032480 A1 | 3/2002 | Spence et al. | |
| 2002/0032481 A1 | 3/2002 | Gabbay | |
| 2002/0042651 A1 | 4/2002 | Liddicoat et al. | |
| 2002/0052651 A1 | 5/2002 | Myers et al. | |
| 2002/0055767 A1 | 5/2002 | Forde et al. | |
| 2002/0055769 A1 | 5/2002 | Wang | |
| 2002/0058995 A1 | 5/2002 | Stevens | |
| 2002/0077696 A1 | 6/2002 | Zadno-Azizi et al. | |
| 2002/0082609 A1 | 6/2002 | Green | |
| 2002/0095173 A1 | 7/2002 | Mazzocchi et al. | |
| 2002/0095209 A1 | 7/2002 | Zadno-Azizi et al. | |
| 2002/0111674 A1 | 8/2002 | Chouinard et al. | |
| 2002/0120328 A1 | 8/2002 | Pathak et al. | |
| 2002/0123802 A1 | 9/2002 | Snyders | |
| 2002/0138138 A1 | 9/2002 | Yang | |
| 2002/0151970 A1 | 10/2002 | Garrison et al. | |
| 2002/0161390 A1 | 10/2002 | Mouw | |
| 2002/0161392 A1 | 10/2002 | Dubrul | |
| 2002/0161394 A1 | 10/2002 | Macoviak et al. | |
| 2002/0165576 A1 | 11/2002 | Boyle | |
| 2002/0177766 A1 | 11/2002 | Mogul | |
| 2002/0183781 A1 | 12/2002 | Casey | |
| 2002/0188341 A1 | 12/2002 | Elliott | |
| 2002/0188344 A1 | 12/2002 | Bolea et al. | |
| 2002/0193871 A1 | 12/2002 | Beyersdorf et al. | |
| 2003/0014104 A1 | 1/2003 | Cribier | |
| 2003/0023303 A1 | 1/2003 | Palmaz et al. | |
| 2003/0028247 A1 | 2/2003 | Cali | |
| 2003/0036791 A1 | 2/2003 | Philipp et al. | |
| 2003/0040736 A1 | 2/2003 | Stevens | |
| 2003/0040771 A1 | 2/2003 | Hyodoh et al. | |
| 2003/0040772 A1 | 2/2003 | Hyodoh et al. | |
| 2003/0040791 A1 | 2/2003 | Oktay | |
| 2003/0040792 A1 | 2/2003 | Gabbay | |
| 2003/0050694 A1 | 3/2003 | Yang et al. | |
| 2003/0055495 A1 | 3/2003 | Pease et al. | |

| | | | | | |
|---|---|---|---|---|---|
| 2003/0057156 A1 | 3/2003 | Peterson et al. | 2004/0210307 A1 | 10/2004 | Khairkhahan |
| 2003/0060844 A1 | 3/2003 | Borillo et al. | 2004/0215331 A1 | 10/2004 | Chew et al. |
| 2003/0069492 A1 | 4/2003 | Abrams et al. | 2004/0215333 A1 | 10/2004 | Duran et al. |
| 2003/0069646 A1* | 4/2003 | Stinson .................. 623/23.7 | 2004/0215339 A1 | 10/2004 | Drasler et al. |
| 2003/0070944 A1 | 4/2003 | Nigam | 2004/0220655 A1 | 11/2004 | Swanson et al. |
| 2003/0100918 A1 | 5/2003 | Duane | 2004/0225321 A1 | 11/2004 | Krolik et al. |
| 2003/0100919 A1 | 5/2003 | Hopkins et al. | 2004/0225353 A1 | 11/2004 | McGuckin, Jr. et al. |
| 2003/0109924 A1 | 6/2003 | Cribier | 2004/0225354 A1 | 11/2004 | Allen et al. |
| 2003/0109930 A1 | 6/2003 | Bluni et al. | 2004/0225355 A1 | 11/2004 | Stevens |
| 2003/0114912 A1 | 6/2003 | Sequin et al. | 2004/0243221 A1 | 12/2004 | Fawzi et al. |
| 2003/0114913 A1 | 6/2003 | Spenser et al. | 2004/0254636 A1 | 12/2004 | Flagle et al. |
| 2003/0125795 A1 | 7/2003 | Pavcnik et al. | 2004/0260390 A1 | 12/2004 | Sarac et al. |
| 2003/0130729 A1 | 7/2003 | Paniagua et al. | 2005/0000858 A1 | 1/2005 | Roovers |
| 2003/0135257 A1 | 7/2003 | Taheri | 2005/0010287 A1 | 1/2005 | Macoviak et al. |
| 2003/0144732 A1 | 7/2003 | Cosgrove et al. | 2005/0021136 A1 | 1/2005 | Xie et al. |
| 2003/0149475 A1 | 8/2003 | Hyodoh et al. | 2005/0033398 A1 | 2/2005 | Seguin |
| 2003/0149476 A1 | 8/2003 | Damm et al. | 2005/0033402 A1 | 2/2005 | Cully et al. |
| 2003/0149478 A1 | 8/2003 | Figulla et al. | 2005/0043711 A1 | 2/2005 | Corcoran et al. |
| 2003/0153974 A1 | 8/2003 | Spenser et al. | 2005/0043757 A1 | 2/2005 | Arad et al. |
| 2003/0165352 A1 | 9/2003 | Ibrahim et al. | 2005/0043790 A1 | 2/2005 | Seguin |
| 2003/0176884 A1 | 9/2003 | Berrada et al. | 2005/0049692 A1 | 3/2005 | Numamoto et al. |
| 2003/0181850 A1 | 9/2003 | Diamond et al. | 2005/0049696 A1 | 3/2005 | Siess et al. |
| 2003/0187495 A1 | 10/2003 | Cully et al. | 2005/0055088 A1 | 3/2005 | Liddicoat et al. |
| 2003/0191516 A1 | 10/2003 | Weldon | 2005/0060029 A1 | 3/2005 | Le et al. |
| 2003/0199913 A1 | 10/2003 | Dubrul et al. | 2005/0065594 A1 | 3/2005 | DiMatteo et al. |
| 2003/0199971 A1 | 10/2003 | Tower et al. | 2005/0075584 A1 | 4/2005 | Cali |
| 2003/0199972 A1 | 10/2003 | Zadno-Azizi et al. | 2005/0075662 A1 | 4/2005 | Pedersen et al. |
| 2003/0208224 A1 | 11/2003 | Broome | 2005/0075712 A1 | 4/2005 | Biancucci et al. |
| 2003/0212429 A1 | 11/2003 | Keegan et al. | 2005/0075717 A1 | 4/2005 | Nguyen et al. |
| 2003/0212452 A1 | 11/2003 | Zadno-Azizi et al. | 2005/0075719 A1 | 4/2005 | Bergheim |
| 2003/0212454 A1 | 11/2003 | Scott et al. | 2005/0075724 A1 | 4/2005 | Svanidze et al. |
| 2003/0216774 A1 | 11/2003 | Larson | 2005/0075730 A1 | 4/2005 | Myers et al. |
| 2003/0225445 A1 | 12/2003 | Derus et al. | 2005/0075731 A1 | 4/2005 | Artof et al. |
| 2003/0229390 A1 | 12/2003 | Ashton et al. | 2005/0084595 A1 | 4/2005 | Shukla |
| 2003/0233117 A1 | 12/2003 | Adams et al. | 2005/0085841 A1 | 4/2005 | Eversull et al. |
| 2004/0034411 A1 | 2/2004 | Quijano et al. | 2005/0085842 A1 | 4/2005 | Eversull et al. |
| 2004/0039436 A1 | 2/2004 | Spenser et al. | 2005/0085843 A1 | 4/2005 | Opolski et al. |
| 2004/0049224 A1 | 3/2004 | Buehlmann et al. | 2005/0085890 A1 | 4/2005 | Rasmussen et al. |
| 2004/0049226 A1 | 3/2004 | Keegan et al. | 2005/0090846 A1 | 4/2005 | Pedersen et al. |
| 2004/0049262 A1 | 3/2004 | Obermiller et al. | 2005/0096692 A1 | 5/2005 | Linder et al. |
| 2004/0049266 A1 | 3/2004 | Anduiza et al. | 2005/0096734 A1 | 5/2005 | Majercak et al. |
| 2004/0059409 A1 | 3/2004 | Stenzel | 2005/0096735 A1 | 5/2005 | Hojeibane et al. |
| 2004/0073198 A1 | 4/2004 | Gilson et al. | 2005/0096736 A1 | 5/2005 | Osse et al. |
| 2004/0082904 A1 | 4/2004 | Houde et al. | 2005/0096738 A1 | 5/2005 | Cali et al. |
| 2004/0082967 A1 | 4/2004 | Broome et al. | 2005/0100580 A1 | 5/2005 | Osborne et al. |
| 2004/0087982 A1 | 5/2004 | Eskuri et al. | 2005/0107822 A1 | 5/2005 | WasDyke |
| 2004/0088045 A1 | 5/2004 | Cox | 2005/0113910 A1 | 5/2005 | Paniagua et al. |
| 2004/0093016 A1 | 5/2004 | Root et al. | 2005/0131438 A1 | 6/2005 | Cohn |
| 2004/0093060 A1 | 5/2004 | Seguin et al. | 2005/0137683 A1 | 6/2005 | Hezi-Yamit et al. |
| 2004/0097788 A1 | 5/2004 | Mourlas et al. | 2005/0137686 A1 | 6/2005 | Salahieh et al. |
| 2004/0098022 A1 | 5/2004 | Barone | 2005/0137687 A1 | 6/2005 | Salahieh et al. |
| 2004/0098098 A1 | 5/2004 | McGuckin, Jr. et al. | 2005/0137688 A1 | 6/2005 | Salahieh et al. |
| 2004/0098099 A1 | 5/2004 | McCullagh et al. | 2005/0137689 A1 | 6/2005 | Salahieh et al. |
| 2004/0098112 A1 | 5/2004 | DiMatteo et al. | 2005/0137690 A1 | 6/2005 | Salahieh et al. |
| 2004/0107004 A1 | 6/2004 | Levine et al. | 2005/0137691 A1 | 6/2005 | Salahieh et al. |
| 2004/0111096 A1 | 6/2004 | Tu et al. | 2005/0137692 A1 | 6/2005 | Haug et al. |
| 2004/0116951 A1 | 6/2004 | Rosengart | 2005/0137693 A1 | 6/2005 | Haug et al. |
| 2004/0117004 A1 | 6/2004 | Osborne et al. | 2005/0137694 A1 | 6/2005 | Haug et al. |
| 2004/0117009 A1 | 6/2004 | Cali et al. | 2005/0137695 A1 | 6/2005 | Salahieh et al. |
| 2004/0122468 A1 | 6/2004 | Yodfat et al. | 2005/0137696 A1 | 6/2005 | Salahieh et al. |
| 2004/0122516 A1 | 6/2004 | Fogarty et al. | 2005/0137697 A1 | 6/2005 | Salahieh et al. |
| 2004/0127936 A1 | 7/2004 | Salahieh | 2005/0137698 A1 | 6/2005 | Salahieh et al. |
| 2004/0127979 A1 | 7/2004 | Wilson et al. | 2005/0137699 A1 | 6/2005 | Salahieh et al. |
| 2004/0133274 A1 | 7/2004 | Webler et al. | 2005/0137701 A1 | 6/2005 | Salahieh et al. |
| 2004/0138694 A1 | 7/2004 | Tran et al. | 2005/0137702 A1 | 6/2005 | Haug et al. |
| 2004/0138742 A1 | 7/2004 | Myers et al. | 2005/0138689 A1 | 6/2005 | Aukerman |
| 2004/0138743 A1 | 7/2004 | Myers et al. | 2005/0143807 A1 | 6/2005 | Pavcnik et al. |
| 2004/0148021 A1 | 7/2004 | Cartledge et al. | 2005/0143809 A1 | 6/2005 | Salahieh et al. |
| 2004/0153094 A1 | 8/2004 | Dunfee et al. | 2005/0165352 A1 | 7/2005 | Henry et al. |
| 2004/0158277 A1 | 8/2004 | Lowe et al. | 2005/0165477 A1 | 7/2005 | Anduiza et al. |
| 2004/0167565 A1 | 8/2004 | Beulke et al. | 2005/0165479 A1 | 7/2005 | Drews et al. |
| 2004/0181140 A1 | 9/2004 | Falwell et al. | 2005/0182486 A1 | 8/2005 | Gabbay |
| 2004/0186558 A1 | 9/2004 | Pavcnik et al. | 2005/0197694 A1 | 9/2005 | Pai et al. |
| 2004/0186563 A1 | 9/2004 | Iobbi | 2005/0197695 A1 | 9/2005 | Stacchino et al. |
| 2004/0193261 A1 | 9/2004 | Berreklouw | 2005/0203549 A1 | 9/2005 | Realyvasquez |
| 2004/0197695 A1 | 10/2004 | Aono | 2005/0203614 A1 | 9/2005 | Forster |
| 2004/0204755 A1 | 10/2004 | Robin | 2005/0203615 A1 | 9/2005 | Forster |
| 2004/0210304 A1 | 10/2004 | Seguin et al. | 2005/0203616 A1* | 9/2005 | Cribier .................. 623/2.11 |
| 2004/0210306 A1 | 10/2004 | Quijano et al. | 2005/0203617 A1 | 9/2005 | Forster et al. |

| | | |
|---|---|---|
| 2005/0203618 A1 | 9/2005 | Sharkawy et al. |
| 2005/0209580 A1 | 9/2005 | Freyman |
| 2005/0228472 A1 | 10/2005 | Case et al. |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240262 A1 | 10/2005 | White |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283231 A1 | 12/2005 | Haug et al. |
| 2005/0283962 A1* | 12/2005 | Boudjemline .................. 29/433 |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0155312 A1 | 7/2006 | Levine et al. |
| 2006/0161249 A1 | 7/2006 | Realyvasquez et al. |
| 2006/0173524 A1 | 8/2006 | Salahieh et al. |
| 2006/0195183 A1 | 8/2006 | Navia et al. |
| 2006/0253191 A1 | 11/2006 | Salahieh et al. |
| 2006/0259134 A1 | 11/2006 | Schwammenthal et al. |
| 2006/0271166 A1 | 11/2006 | Thill et al. |
| 2006/0287668 A1 | 12/2006 | Fawzi et al. |
| 2007/0010876 A1 | 1/2007 | Salahieh |
| 2007/0010877 A1 | 1/2007 | Salahieh |
| 2007/0016286 A1 | 1/2007 | Herrmann et al. |
| 2007/0055340 A1 | 3/2007 | Pryor |
| 2007/0061008 A1 | 3/2007 | Salahieh |
| 2007/0112355 A1 | 5/2007 | Salahieh |
| 2007/0118214 A1 | 5/2007 | Salahieh |
| 2007/0162107 A1 | 7/2007 | Haug |
| 2007/0173918 A1 | 7/2007 | Dreher et al. |
| 2007/0203503 A1 | 8/2007 | Salahieh |
| 2007/0244552 A1 | 10/2007 | Salahieh |
| 2007/0288089 A1 | 12/2007 | Gurskis et al. |
| 2008/0009940 A1 | 1/2008 | Cribier |
| 2008/0082165 A1 | 4/2008 | Wilson et al. |
| 2008/0125859 A1 | 5/2008 | Salahieh |
| 2008/0188928 A1 | 8/2008 | Salahieh |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234814 A1 | 9/2008 | Salahieh et al. |
| 2008/0269878 A1 | 10/2008 | Iobbi |
| 2008/0288054 A1 | 11/2008 | Pulnev et al. |
| 2009/0005863 A1 | 1/2009 | Goetz |
| 2009/0030512 A1 | 1/2009 | Thielen et al. |
| 2009/0054969 A1 | 2/2009 | Salahieh |
| 2009/0076598 A1 | 3/2009 | Salahieh |
| 2009/0171456 A1 | 7/2009 | Kveen et al. |
| 2009/0222076 A1 | 9/2009 | Figulla et al. |
| 2009/0264759 A1 | 10/2009 | Byrd |
| 2009/0264997 A1 | 10/2009 | Salahieh |
| 2009/0299462 A1 | 12/2009 | Fawzi et al. |
| 2010/0049313 A1 | 2/2010 | Alon et al. |
| 2010/0121434 A1 | 5/2010 | Paul |
| 2010/0219092 A1 | 9/2010 | Salahieh et al. |
| 2010/0280495 A1 | 11/2010 | Paul |

FOREIGN PATENT DOCUMENTS

| | | |
|---|---|---|
| DE | 19532846 | 3/1997 |
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049814 | 4/2002 |
| DE | 10049815 | 10/2005 |
| EP | 0103546 | 5/1988 |
| EP | 0144167 | 11/1989 |
| EP | 0409929 | 4/1997 |
| EP | 0409929 B1 | 4/1997 |
| EP | 0850607 | 7/1998 |
| EP | 0597967 | 12/1999 |
| EP | 1000590 | 5/2000 |
| EP | 1000590 A1 | 5/2000 |
| EP | 1057459 | 12/2000 |
| EP | 1057460 | 12/2000 |
| EP | 1088529 | 4/2001 |
| EP | 0937439 | 9/2003 |
| EP | 0937439 B1 | 9/2003 |
| EP | 1340473 A2 | 9/2003 |
| EP | 1356793 | 10/2003 |
| EP | 1042045 | 5/2004 |
| EP | 1042045 B1 | 5/2004 |
| EP | 0819013 | 6/2004 |
| EP | 1435879 | 7/2004 |
| EP | 1439800 | 7/2004 |
| EP | 1472996 | 11/2004 |
| EP | 1229864 B1 | 4/2005 |
| EP | 1430853 A2 | 6/2005 |
| EP | 1059894 B1 | 7/2005 |
| EP | 1551274 | 7/2005 |
| EP | 1551336 | 7/2005 |
| EP | 1078610 B1 | 8/2005 |
| EP | 1562515 | 8/2005 |
| EP | 1570809 | 9/2005 |
| EP | 1576937 A2 | 9/2005 |
| EP | 1582178 A2 | 10/2005 |
| EP | 1582179 A2 | 10/2005 |
| EP | 1469797 | 11/2005 |
| EP | 1589902 | 11/2005 |
| EP | 1600121 | 11/2005 |
| EP | 1156757 B1 | 12/2005 |
| EP | 1616531 | 1/2006 |
| EP | 1605871 | 7/2008 |
| FR | 2788217 | 1/1999 |
| GB | 2056023 | 3/1981 |
| GB | 2398245 | 8/2004 |
| SU | 1271508 | 11/1986 |
| SU | 1371700 | 2/1988 |
| WO | 9117720 | 11/1991 |
| WO | 9217118 | 10/1992 |
| WO | 9301768 | 2/1993 |
| WO | WO 93/15693 | 8/1993 |
| WO | WO 95/04556 | 2/1995 |
| WO | WO 95/29640 | 11/1995 |
| WO | WO 96/14032 | 5/1996 |
| WO | WO 96/24306 A1 | 8/1996 |
| WO | 9829057 | 7/1998 |
| WO | WO 98/36790 | 8/1998 |
| WO | WO 98/50103 A1 | 11/1998 |
| WO | WO 98/57599 A2 | 12/1998 |
| WO | 9933414 | 7/1999 |
| WO | 9940964 | 8/1999 |
| WO | 9947075 | 9/1999 |
| WO | WO 99/44542 A2 | 9/1999 |
| WO | WO 00/09059 | 2/2000 |
| WO | 0041652 | 7/2000 |
| WO | 0044211 | 7/2000 |
| WO | 0044311 | 8/2000 |
| WO | 0047139 | 8/2000 |
| WO | 1145874 | 8/2000 |
| WO | WO 00/44308 | 8/2000 |
| WO | WO 00/44313 | 8/2000 |
| WO | WO 00/49970 A1 | 8/2000 |
| WO | WO 00/67661 | 11/2000 |
| WO | WO 01/05331 | 1/2001 |
| WO | 0110343 | 2/2001 |
| WO | WO 01/08596 A1 | 2/2001 |
| WO | WO 01/10320 A1 | 2/2001 |
| WO | WO 01/10343 A1 | 2/2001 |
| WO | 0135870 | 5/2001 |
| WO | WO 01/35870 | 5/2001 |
| WO | 0149213 | 7/2001 |
| WO | 0154625 | 8/2001 |
| WO | 0162189 | 8/2001 |
| WO | 0164137 | 9/2001 |
| WO | WO 01/64137 | 9/2001 |
| WO | 0197715 | 12/2001 |
| WO | 0241789 | 5/2002 |
| WO | WO 02/36048 | 5/2002 |
| WO | WO 02/41789 A2 | 5/2002 |
| WO | 0243620 | 6/2002 |
| WO | 0247575 | 6/2002 |
| WO | WO 02/100297 | 12/2002 |

| | | |
|---|---|---|
| WO | WO 03/003943 | 1/2003 |
| WO | WO 03/003949 | 1/2003 |
| WO | WO 03/011195 | 2/2003 |
| WO | 03030776 | 4/2003 |
| WO | 03094793 | 11/2003 |
| WO | 03094797 | 11/2003 |
| WO | WO 03/015851 | 11/2003 |
| WO | WO 2004/014256 A1 | 2/2004 |
| WO | 2004019811 A2 | 3/2004 |
| WO | WO 2004/019811 | 3/2004 |
| WO | WO 2004/023980 | 3/2004 |
| WO | WO 2004/026117 A2 | 4/2004 |
| WO | WO 2004/041126 | 5/2004 |
| WO | WO 2004/047681 A1 | 6/2004 |
| WO | 2004058106 | 7/2004 |
| WO | WO 2004/066876 A1 | 8/2004 |
| WO | WO 2004/082536 A1 | 9/2004 |
| WO | 2004089250 | 10/2004 |
| WO | 2004089253 | 10/2004 |
| WO | 2004093728 | 11/2004 |
| WO | 2004105651 | 12/2004 |
| WO | 2005002466 | 1/2005 |
| WO | 2005004753 | 1/2005 |
| WO | 2005009285 | 2/2005 |
| WO | 2005011534 | 2/2005 |
| WO | 2005011535 | 2/2005 |
| WO | 2005023155 | 3/2005 |
| WO | 2005027790 | 3/2005 |
| WO | 2005046528 | 5/2005 |
| WO | 2005046529 | 5/2005 |
| WO | 2005048883 | 6/2005 |
| WO | 2005/062980 | 7/2005 |
| WO | 2005065585 | 7/2005 |
| WO | 2005084595 | 9/2005 |
| WO | 2005087140 | 9/2005 |
| WO | 2005096993 | 10/2005 |
| WO | 2006009690 | 1/2006 |
| WO | 2006027499 | 3/2006 |
| WO | 2006138391 | 12/2006 |
| WO | 2007033093 | 3/2007 |
| WO | 2007035471 | 3/2007 |
| WO | 2007044285 | 4/2007 |
| WO | 2007053243 | 5/2007 |
| WO | 2007058847 | 5/2007 |
| WO | 2007092354 | 8/2007 |
| WO | 2007097983 | 8/2007 |
| WO | 2010042950 | 4/2010 |

OTHER PUBLICATIONS

Salahieh, et al., U.S. Appl. No. 12/269,213 entitled "Everting heart valve," filed Nov. 12, 2008.
Paul et al.; U.S. Appl. No. 12/578,463 entitled "Medical Devices and Delivery Systems for Delivering Medical Devices," filed Oct. 13, 2009.
Paul et al.; U.S. Appl. No. 12/578,447 entitled "Medical Devices and Delivery Systems for Delivering Medical Devices," filed Oct. 13, 2009.
Salahieh, et al; U.S. Appl. No. 11/732,906 entitled "Assessing the location and performance of replacement heart valves," filed Apr. 4, 2007.
Salahieh, et al., U.S. Appl. No. 11/274,889, entitled "Medical implant deployment tool," filed Nov. 14, 2005.
Salahieh, et al., U.S. Appl. No. 11/314,183, entitled "Medical Device Delivery," filed Dec. 20, 2005.
Salahieh, et al., U.S. Appl. No. 11/314,969, entitled "Methods and Apparatus for Performing Valvuloplasty," filed Dec. 20, 2005.
Salahieh, et al., U.S. Appl. No. 11/275,913, entitled "Two-Part Package for Medical Implant," filed Feb. 2, 2006.
Salahieh, et al., U.S. Appl. No. 11/531,980, entitled "Externally expandable heart valve anchor and method," filed Sep. 14, 2006.
Salahieh, et al., U.S. Appl. No. 11/532,019, entitled "Methods and apparatus for endovascularly replacing heart valve," filed Sep. 14, 2006.
Salahieh, et al; U.S. Appl. No. 11/706,549, entitled "Systems and Methods for Delivering a Medical Implant," filed Feb. 14, 2007.

Andersen, H.R. et al. "Transluminal implantation of artificial heart valves. Description of a new expandable aortic valve and initial results with implantation by catheter technique in closed chest pigs." Euro. Heart J. 1992; 13:704-708.
Atwood, A. et al. "Insertion of Heart Valves by Catheterization." Project Supervised by Prof. S. Muftu of Northeaster University 2001-2002: 36-40.
Bodnar, E. et al. Replacement Cardiac Valves R Chapter 13: Extinct cardiac valve prostheses. Pergamon Publishing Corporation. New York, 1991: 307-322.
Boudjemline, Y. et al. "Percutaneous implantation of a biological valve in the aorta to treat aortic valve insufficiency—a sheep study." Med Sci. Monit. 2002; vol. 8, No. 4: BR113-116.
Boudjemline, Y. et al. "Percutaneous implantation of a valve in the descending aorta in lambs." Euro. Heart J. 2002; 23: 1045-1049.
Boudjemline, Y. et al. "Percutaneous valve insertion: A new approach?" J. of Thoracic and Cardio. Surg. 2003; 125(3): 741-743.
Boudjemline, Y. et al. "Steps Toward Percutaneous Aortic Valve Replacement." Circulation. 2002; 105: 775-778.
Cribier, A., et al. "Percutaneous Transcatheter Implantation of an Aortic Valve Prosthesis for Calcific Aortic Stenosis: First Human Case Description." Circulation. 2002; 106: 3006-3008.
Cribier, A., et al. "Percutaneous Transcatheter Implantation of an Aortic Valve Prosthesis for Calcific Aortic Stenosis: First Human Case." Percutaneous Valve Technologies, Inc. 2002: 16 pages.
Ferrari, M. et al. "Percutaneous transvascular aortic valve replacement with self expanding stent-valve device." Poster from the presentation given at SMIT 2000, 12th International Conference. Sep. 5, 2000.
Knudsen, L. L. et al. "Catheter-implanted prosthetic heart valves." Int'l J. of Art. Organs. 1993; 16(5): 253-262.
Kort, S. et al. "Minimally invasive aortic valve replacement: Echocardiographic and clinical results." Am. Heart J. 2001; 142(3): 476-481.
Love, C. et al. "The Autogenous Tissue Heart Valve: Current Status." Journal of Cardiac Surgery. 1991; 6(4): 499-507.
Lutter, G. et al. "Percutaneous aortic valve replacement: An experimental study. I. Studies on implantation." J. of Thoracic and Cardio. Surg. 2002; 123(4): 768-776.
Moulopoulos, S. D. et al. "Catheter-Mounted Aortic Valves." Annals of Thoracic Surg. 1971; 11(5): 423-430.
Paniagua, D. et al. "Percutaneous heart valve in the chronic in vitro testing model." Circulation. 2002; 106: e51-e52.
Pavcnik, D. et al. "Percutaneous bioprosthetic venous valve: A long-term study in sheep." J. of Vascular Surg. 2002; 35(3): 598-603.
Phillips, S. J. at al. "A Temporary Catheter-Tip Aortic Valve: Hemodynamic Effects on Experimental Acute Aortic Insufficiency." Annals of Thoracic Surg. 1976; 21(2): 134-136.
Sochman, J. et al. "Percutaneous Transcatheter Aortic Disc Valve Prosthesis Implantation: A Feasibility Study." Cardiovasc. Intervent. Radiol. 2000; 23: 384-388.
Van Herwerden, L. A. et al., "Percutaneous valve implantation: back to the future?" Euro. Heart J. 2002; 23(18): 1415-1416.
Zhou, J. Q. et al. "Self-expandable valved stent of large size: off-bypass implantation in pulmonary position." Eur. J. Cardiothorac. 2003; 24: 212-216.
Haug et al.; U.S. Appl. No. 12/028,452 entitled "Methods and apparatus for endovascularly replacing a patient's heart valve," filed Feb. 8, 2008.
Haug et al.; U.S. Appl. No. 12/492,512 entitled "Everting Heart Valve," filed Jun. 26, 2009.
Salahieh, et al., U.S. Appl. No. 12/132,304 entitled "Low profile heart valve and delivery system," filed Jun. 3, 2008.
Boudjemline, Y. et al. "Percutaneous pulmonary valve replacement in a large right ventricular outflow tract: an experimental study." Journal of the Americal College of Cardiology. 2004; vol. 43(6): 1082-1087.
Cribier, A. et al. "Early Experience with Percutaneous Transcatheter Implantation of Heart Valve Prosthesis for the Treatment of End-Stage Inoperable Patients with Calcific Aortic Stenosis." J. of Am. Coll. of Cardio. 2004; 43(4): 698-703.
Hijazi, Z.M. "Transcatheter Valve Replacement: A New Era of Percutaneous Cardiac Intervention Begins." J. of Am. College of Cardio. 2004; 43(6): 1088-1089.

Huber, C.H. et al. "Do valved stents compromise coronary flow?" European Journal of Cardio-thoracic Surgery. 2004; vol. 25: 754-759.

Paniagua, D. et al. Heart Watch (2004). Texas Heart Institute. Spring, 2004 Edition: 8 pages.

Stuart, M. "In Heart Valves, A Brave, New Non-Surgical World." Start-Up. 2004: 9-17.

Vahanian, A. et al. "Percutaneous Approaches to Valvular Disease." Circulation. 2004; 109: 1572-1579.

A Matter of Size, Treiennial Review of the National Nanotechnology Initiative, 2006, v-13, The National Academies Press, Washington, DC htt://www.Nap.edu/cataog/11752.html.

Ferrari, M. et al., "Percutaneous transvascular aortic valve replacement with self expanding stent-valve device." Poster from the perdetation given at SMIT 2000, 12th International Conference (Sep. 5, 2000).

VentureBeatProfiles, Claudio Argento, Jan. 7, 2010, http://venturebeatprofiles.com/person/profile/claudio-argento.

Heart Valve Materials—Bovine (cow), Equine & Porcine Pericardium, Maverick Biosciences Pty. Ltd, Jan. 7, 2011, http://www.maverickbio.com/biological-medical-device-materials.php?htm.

Hijazi, Z.M., Transcatheter Valve Replacement: A New Era of Percutaneous Cardiac Intervention Begins. J. of Am. College of Cardio (2004) 43:6, 1088-1089.

Hourihan, Maribeth, et al., Transcatheter Umbrella Closure of Valvular and Paravalvular Leaks, Nov. 15, 1992, 1371-7, vol. 20, No. 6, JACC, Boston Massachusetts.

J.C. Laborde, Percutaneous implantation of the corevalve aortic valve prosthesis for patients presenting high risk for surgical valve replacement, 2006, 472-474, EuroIntervention.

Kort, S. et al., "Minimally invasive aortic valve replacement". Echocardiographic and clinical results Am. Heart J. 2001;142(3): 476-481.

Love, C. et al., The Autogenous Tissue Heart Valve: Current Status, Journal of Cardiac Surgery.(1991)6:4, 499-507.

Lutter, G. et al., "Percutaneous aortic valve replacement: An experimental study. I. Studies of implantation," J. Thoracic and Cardio. Surg. (2002)123:4, 768-776.

Paniagua, D. et al., "Percutaneous heart valve in the chronic in vitro testing model" Circulation (2002) 106:e51-e52, American Heart Association, Inc.

Stuart, M., "In Heart Valves, A Brave, New Non-Surgical World." Start-Up (2004) 9-17.

Topol, Eric J., M.D., Percutaneous Expandable Prosthetic Valves, Textbook of Interventional Cardiology, 1994, 1268-1276, vol. 2, W.B. Saunders Company, Philadelphia.

Van Herwerden, L.A. et al., "Percutaneous Valve Implantation: back to the furture?"Euro Heart J. (2002) 23:18, 1415-1416.

Cunanan, Crystal, M., M.S., et al., Tissue Characterization and Calcification Potential of Commercial Bioprosthetic Heat Valves, 2001, S417-21, Elsevier Science Inc.

H.R. Cunliffe, et al., Glutaraldehyde Inactivation of Exotic Animal Viruses in Swine Heart Tissue, May 1979, 1044-1046, vol. 37, No. 5, Applied and Enviormental Microbiology, Greenport, New York.

Levy, Charles, M.D., Mycrobacterium Chelonei Infection of Porcine Heart Valves, Sep. 22, 1977, vol. 297, No. 12, The New England Journal of Medicine, Washington, D.C.

Pericardial Heart Valve, Edwards Lifesciences, Cardiovascular Surpgery FAQ, 11114/2010, http://www.edwards.com/products/cardiovascularsurgeryfaq.htm Aug. 19, 2011, Supplemental Search Report form EP Patent Office, EP Application No. 04813777.2.

Aug. 19, 2011, Supplemental Search Report form EP Patent Office, EP Application No. 04815634.3.

EP Search Report mailed Aug. 10, 2011 for EP Application No.: 06824992.9.

Sochman, J. et al., "Percutaneous Transcatheter Aortic Disc Valve prothesis Implantation: A Feasibility Study". Cardiovasc. Intervent. Radiol (2000) 23, 384-388.

Stassano, Paolo, Mid-term results of the valve-on-valve technique for bioprosthetic failure, 2000, 453-457, European Journal Carsio-thoracic Suegery.

Vahanian, A. et al., "Percutaneous Approaches to Valvular Disease." Circulation (2004) 109, 1572-1579.

Zhou, J.Q. et al., "Self-Expandable valve stent of large size: off-bypass implantation on pulmonary position". Eur. J. Cardiothorac (2003) 24, 212-216.

Atwood, A. et al., "Insertion of Heart Valves by Catherization". The Capstone Design Report. MIME 1501-1502. Technical Design Report. Northeastern University. Nov. 5, 2007, pp. 1-93.

Helmus, M.N., Mechanical and bioprosthetic heart valves in biomaterials for artificial organs, 114-162, Wooodhead Publishing Limited, 2011.

Southern Lights Biomaterials Homepage, viewed on Jan. 7, 2011, http://www.slv.co.nz/.

Examiner's First Report on AU Patent Application No. 2011202667, issued on May 17, 2012.

* cited by examiner

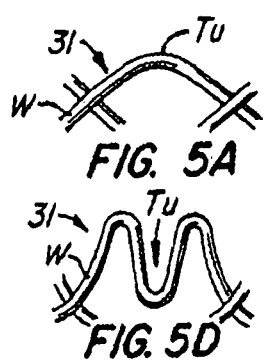
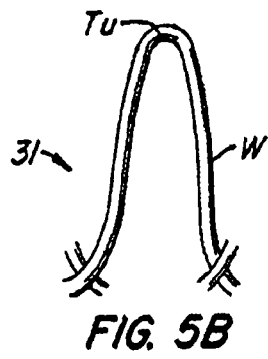
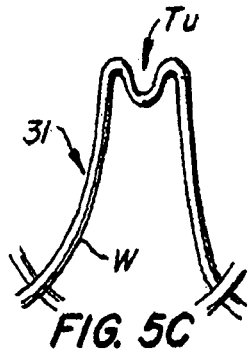
FIG. 5A   FIG. 5B   FIG. 5C
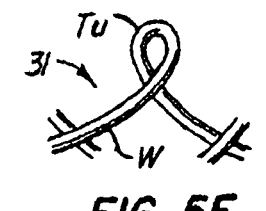
FIG. 5D
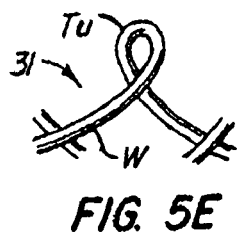
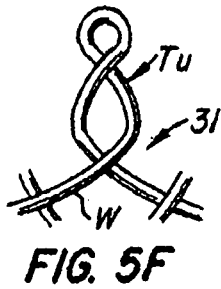
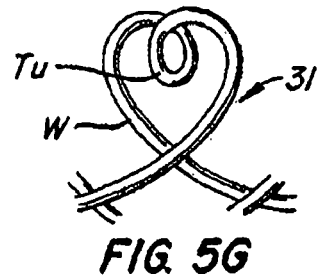
FIG. 5E   FIG. 5F   FIG. 5G
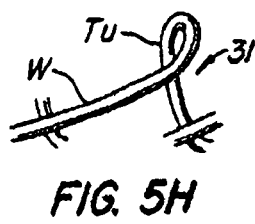
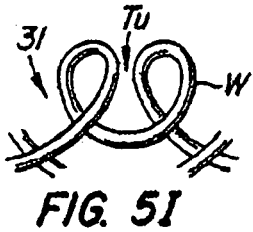
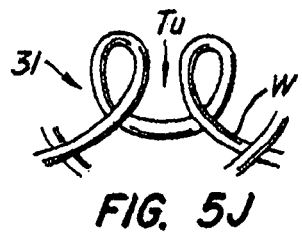
FIG. 5H   FIG. 5I   FIG. 5J
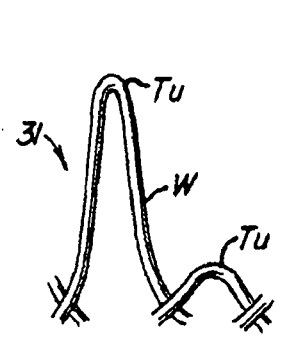
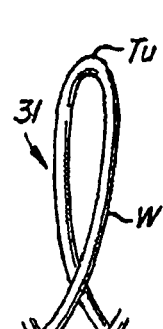
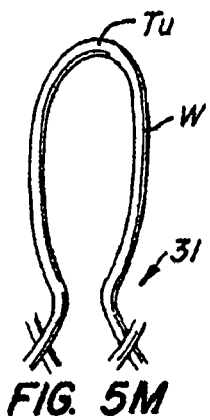
FIG. 5K   FIG. 5L   FIG. 5M

METHODS AND APPARATUS FOR ENDOVASCULARLY REPLACING A PATIENT'S HEART VALVE

CROSS REFERENCE

This application is a continuation of pending U.S. application Ser. No. 10/893,151, filed Jul. 15, 2004 now abandoned; which application is a continuation-in-part of pending U.S. application Ser. No. 10/746,280, filed Dec. 23, 2003, currently pending. These applications are incorporated by reference as if fully set forth herein.

BACKGROUND OF THE INVENTION

Heart valve surgery is used to repair or replace diseased heart valves. Valve surgery is an open-heart procedure conducted under general anesthesia. An incision is made through the patient's sternum (sternotomy), and the patient's heart is stopped while blood flow is rerouted through a heart-lung bypass machine.

Valve replacement may be indicated when there is a narrowing of the native heart valve, commonly referred to as stenosis, or when the native valve leaks or regurgitates. When replacing the valve, the native valve is excised and replaced with either a biologic or a mechanical valve. Mechanical valves require lifelong anticoagulant medication to prevent blood clot formation, and clicking of the valve often may be heard through the chest. Biologic tissue valves typically do not require such medication. Tissue valves may be obtained from cadavers or may be porcine or bovine, and are commonly attached to synthetic rings that are secured to the patient's heart.

Valve replacement surgery is a highly invasive operation with significant concomitant risk. Risks include bleeding, infection, stroke, heart attack, arrhythmia, renal failure, adverse reactions to the anesthesia medications, as well as sudden death. Two to five percent of patients die during surgery.

Post-surgery, patients temporarily may be confused due to emboli and other factors associated with the heart-lung machine. The first 2-3 days following surgery are spent in an intensive care unit where heart functions can be closely monitored. The average hospital stay is between 1 to 2 weeks, with several more weeks to months required for complete recovery.

In recent years, advancements in minimally invasive surgery and interventional cardiology have encouraged some investigators to pursue percutaneous replacement of the aortic heart valve. See, e.g., U.S. Pat. No. 6,168,614. In many of these procedures, the replacement valve is deployed across the native diseased valve to permanently hold the valve open, thereby alleviating a need to excise the native valve and to position the replacement valve in place of the native valve.

In the endovascular aortic valve replacement procedure, accurate placement of aortic valves relative to coronary ostia and the mitral valve is critical. Some self-expanding valve anchors have had very poor accuracy in deployment, however. In a typical deployment procedure, the proximal end of the stent is not released from the delivery system until accurate placement is verified by fluoroscopy. The stent often jumps to another position once released, making it impossible to know where the ends of the stent will be after, release with respect to the native valve, the coronary ostia and the mitral valve.

Also, visualization of the way the new valve is functioning prior to final deployment is very desirable. Due to the jumping action of some self-expanding anchors, and because the replacement valve is often not fully functional before final deployment, visualization of valve function and position prior to final and irreversible deployment is often impossible with these systems.

Another drawback of prior art self-expanding replacement heart valve systems is their relative lack of radial strength. In order for self-expanding systems to be easily delivered through a delivery sheath, the metal needs to flex and bend inside the delivery catheter without being plastically deformed. Expandable stent designs suitable for endovascular delivery for other purposes may not have sufficient radial strength to serve as replacement heart valve anchors. For example, there are many commercial arterial stent systems that apply adequate radial force against the artery wall to treat atherosclerosis and that can collapse to a small enough of a diameter to fit inside a delivery catheter without plastically deforming. However when the stent has a valve fastened inside it, and that valve must reside within the heart, as is the case in aortic valve replacement, the anchoring of the stent to vessel walls takes significantly more radial force, especially during diastole. The force to hold back arterial pressure and prevent blood from going back inside the ventricle during diastole will be directly transferred to the stent/vessel wall interface. Therefore, the amount of radial force required to keep the self-expanding stent/valve in contact with the vessel wall and not sliding is much higher than in stents that do not have valves inside of them. Moreover, a self-expanding stent without sufficient radial force will end up dilating and contracting with each heartbeat, thereby distorting the valve, affecting its function and possibly causing it to migrate and dislodge completely. Simply increasing strut thickness of the self-expanding stent is not a good solution as it increases profile and/or a risk of plastic deformation of the self-expanding stent.

In view of drawbacks associated with previously known techniques for endovascularly replacing a heart valve, it would be desirable to provide methods and apparatus that overcome those drawbacks.

SUMMARY OF THE INVENTION

The present invention relates to an apparatus for replacing a patient's native heart valve. The apparatus comprises an anchor having an expandable braid adapted for endovascular delivery. The anchor is further adapted for expansion via active foreshortening at an anchor site within the native valve. The apparatus also includes a replacement valve adapted to be secured within the patient. In some embodiments, the anchor braid is further adapted to remain substantially undeformed in response to a pressure up to 0.5 atm or 2 atm directed substantially radially inward toward the central axis. In some embodiments, the anchor braid comprises a first region and a second region having a diameter larger than a diameter of the first region when the anchor is expanded. In some embodiments, the anchor braid is configured to have an expanded shape that is radially symmetrical, bilaterally symmetrical, or asymmetrical. In some embodiments, the anchor comprises first and second wires, the first wire having a diameter smaller than a diameter of the second wire. In some embodiments, the anchor comprises first and second wires formed from different materials. In some embodiments, the anchor has a collapsed delivery configuration, an at-rest configuration and an expanded deployed configuration.

In some embodiments, the apparatus herein further comprises a lock or a plurality of locks configured to maintain expansion of the braid. In some embodiments, the apparatus herein further comprises a valve support adapted to support the replacement valve within the anchor. In some embodiments, the anchor herein comprises a distal deployment system interface at a distal end of the anchor, the distal deployment system interface being adapted to permit a deployment system to apply a proximally directed force on the distal end of the anchor. In some embodiments, the anchor comprises a proximal deployment system interface at a proximal end of the anchor, the proximal deployment system interface being adapted to permit a deployment system to apply a distally directed force on the proximal end of the anchor.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 illustrates the apparatus in a collapsed delivery configuration within a delivery system. FIG. 1B illustrates the apparatus in an expanded configuration partially deployed from the delivery system.

DETAILED DESCRIPTION OF THE INVENTION

The present invention relates to a delivery system, apparatus and methods for endovascularly delivering and deploying an aortic prosthesis within a patient's native heart valve, referred to here out as replacing a patients heart valve. The delivery system includes a sheath assembly and a guide wire for placing the apparatus endovascularly within a patient and a user control allowing manipulation of the aortic prosthesis. The apparatus includes an anchor and a replacement valve. The anchor includes an expandable braid. In preferred embodiments, the expandable braid includes closed edges. The replacement valve is adapted to be secured within the anchor, and as such, be delivered endovascularly to patient's heart to replace the patient's native heart valve. More preferably, the apparatus and methods of the present invention contemplate the replacement of a patient's aortic valve.

Figure 1A:
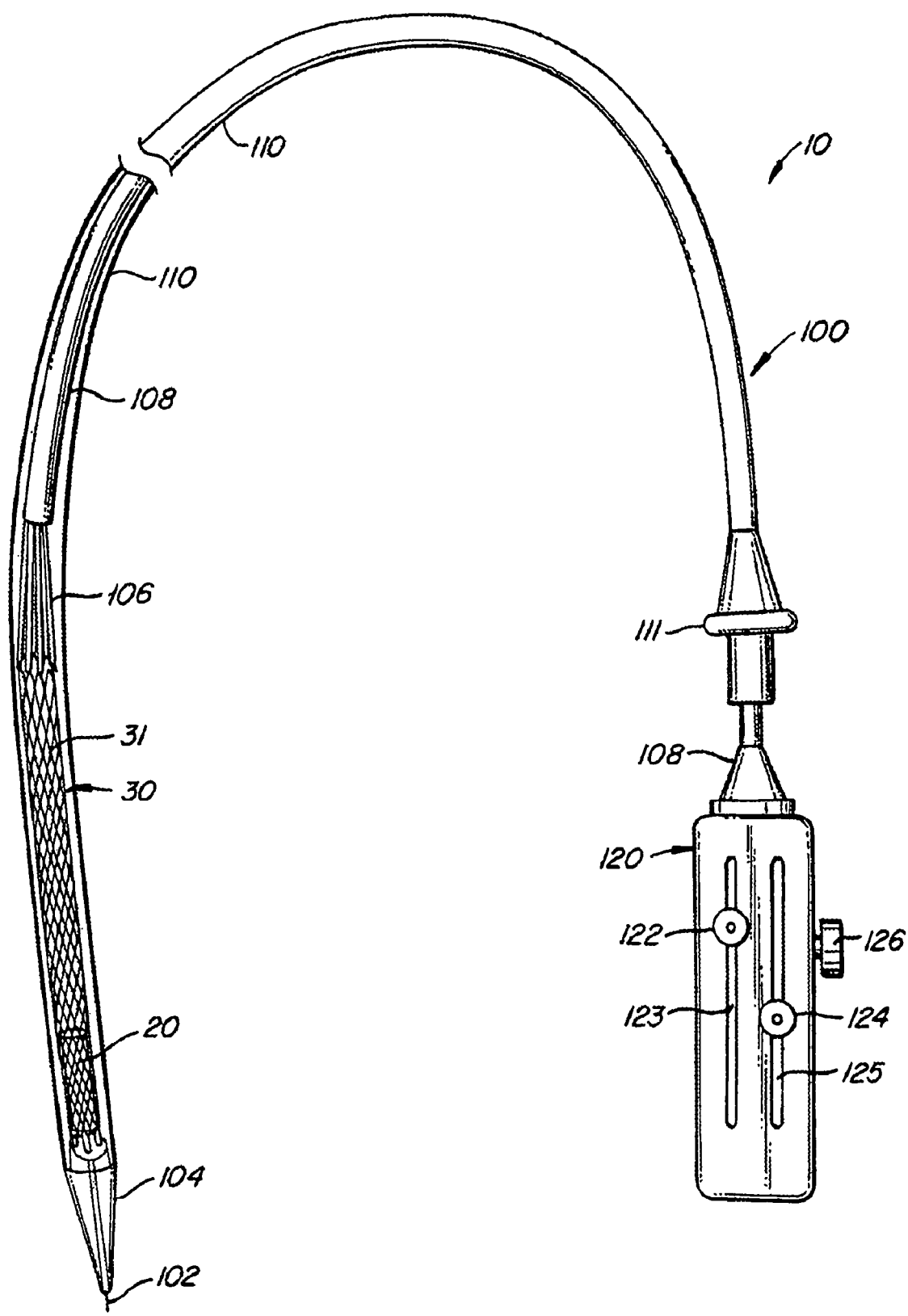
FIGS. 1A and 1B are schematic top views of an anchor and valve apparatus in accordance with the present invention.
Figure 11A:
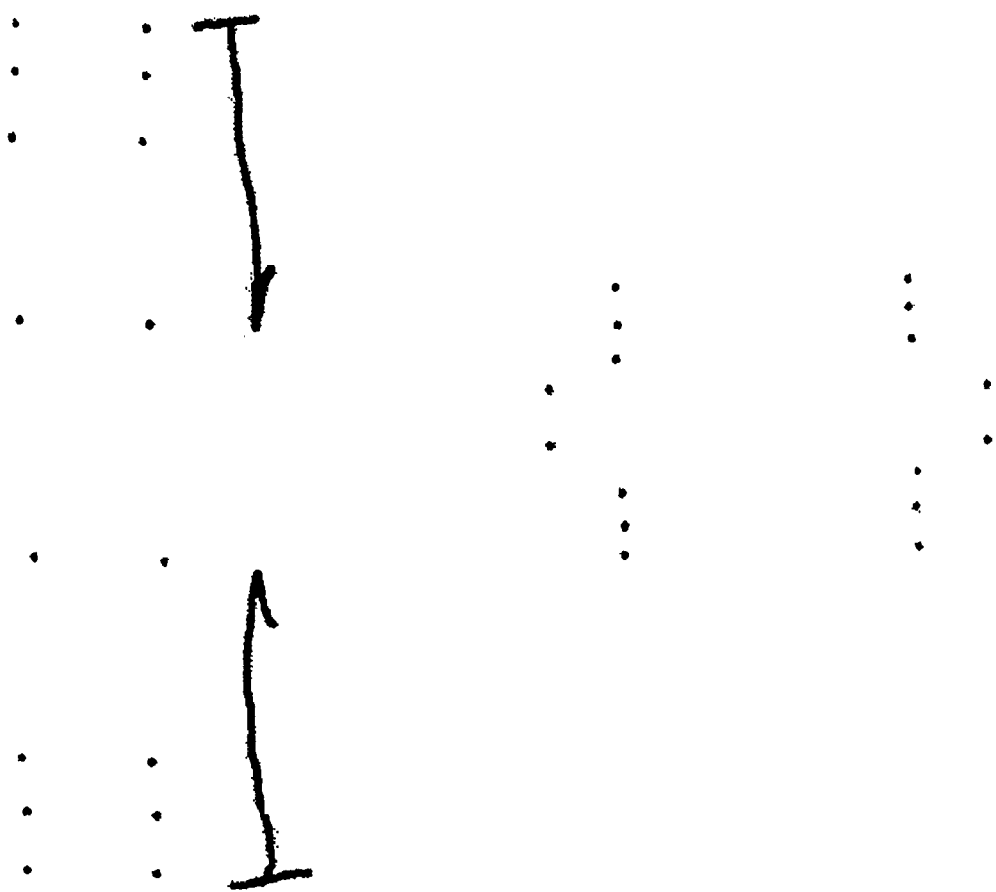
FIGS. 11A-11E are schematic side views of various braided anchor configurations.
Figure 11B:

FIGS. 11A and 11B illustrate one embodiment of a delivery system and apparatus in accordance with the present invention is described. As illustrated by FIG. 1A, apparatus 10 may be collapsed for delivery within a delivery system 100. Delivery system 100 includes a guidewire 102, a nosecone 104, control tubes 106 coupled to a multi-lumen shaft 108, an external sheath 110 having a proximal handle 111, and a control handle 120. Delivery system 100 further comprises distal region control wires (not shown), which pass through one or more lumens of shaft 108 and are reversibly coupled to posts 32 of anchor 30 for manipulating a distal region of apparatus 10. The delivery system also comprises proximal region control wires 112 that pass through one or more lumens of shaft 108 and control tubes 106 (also known as fingers) to reversibly couple the control tubes to a proximal region of anchor 30. The control wires may comprise, for example, strands of suture, or metal or polymer wires.

Control handle 120 is coupled to multi-lumen shaft 108. A knob 122 disposed in slot 123 is coupled to the distal region control wires for controlling movement of the distal region of apparatus 10. Likewise, a knob 124 disposed in slot 125 is coupled to proximal region control wires 112 for control of the proximal region of apparatus 10. Handle 120 may also have a knob 126 for, e.g., decoupling the proximal and/or distal region control wires from apparatus 10, or for performing other control functions.

Figures 1B, 2A:
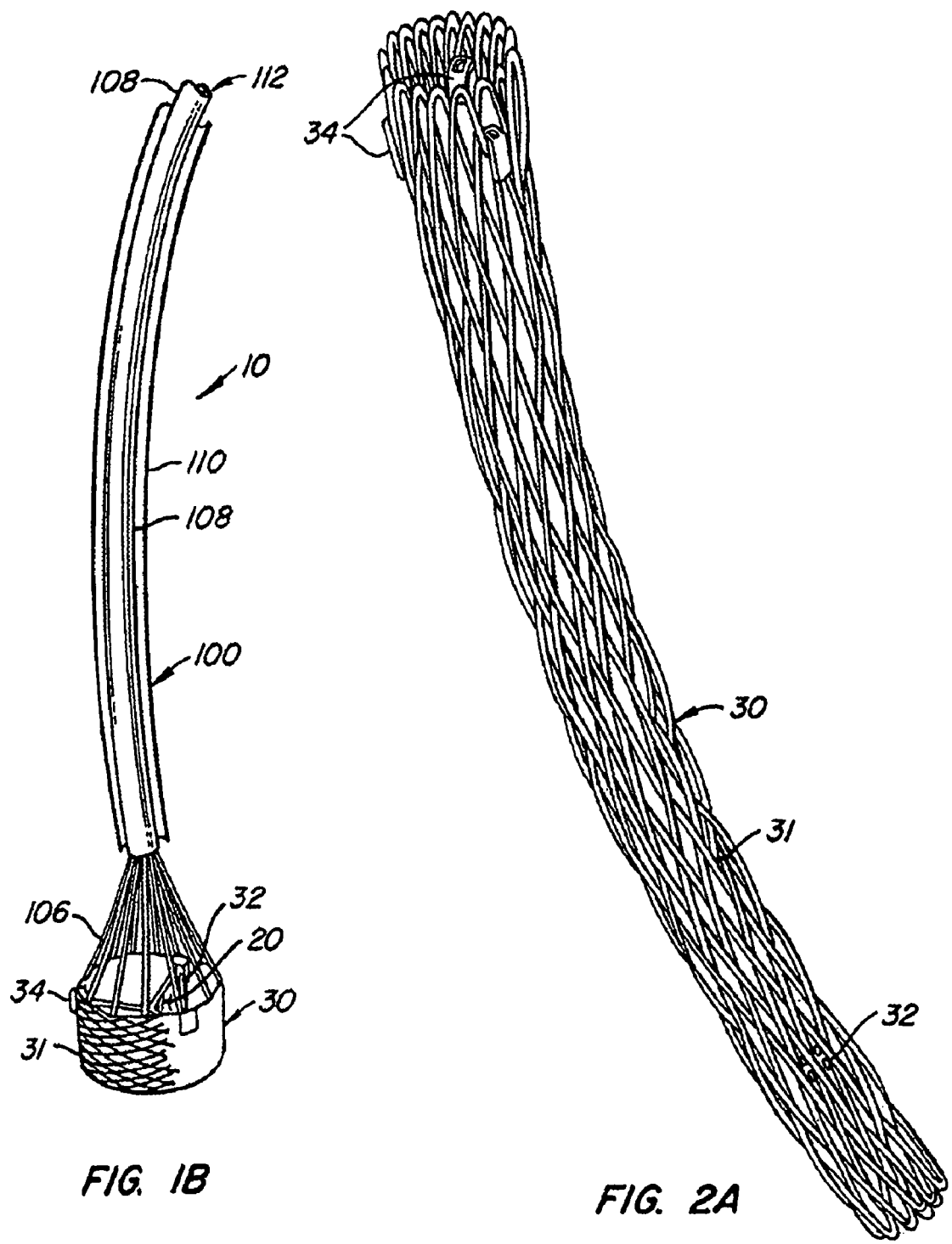
FIGS. 2A-2F are schematic isometric views detailing an anchor of the apparatus of FIG. 1 in the collapsed delivery configuration and the expanded deployed configuration, as well as the full apparatus in the deployed configuration.

Apparatus 10 has an anchor 30 and a replacement valve 20. Anchor 30 preferably comprises a braid. Such braid can have closed ends at either or both its ends. Replacement valve 20 is preferably coupled to the anchor along posts 32. Post 32 therefore, may function as valve support and may be adapted to support the replacement valve within the anchor. In the embodiment shown, there are three posts, corresponding to the valve's three commissure points. The posts can be attached to braid portion of anchor 30. The posts can be attached to the braid's distal end, as shown in FIG. 2A, central region, or proximal end. Replacement valve 20 can be composed of a synthetic material and/or may be derived from animal tissue. Replacement valve 20 is preferably configured to be secured within anchor 30.

Figure 2B:
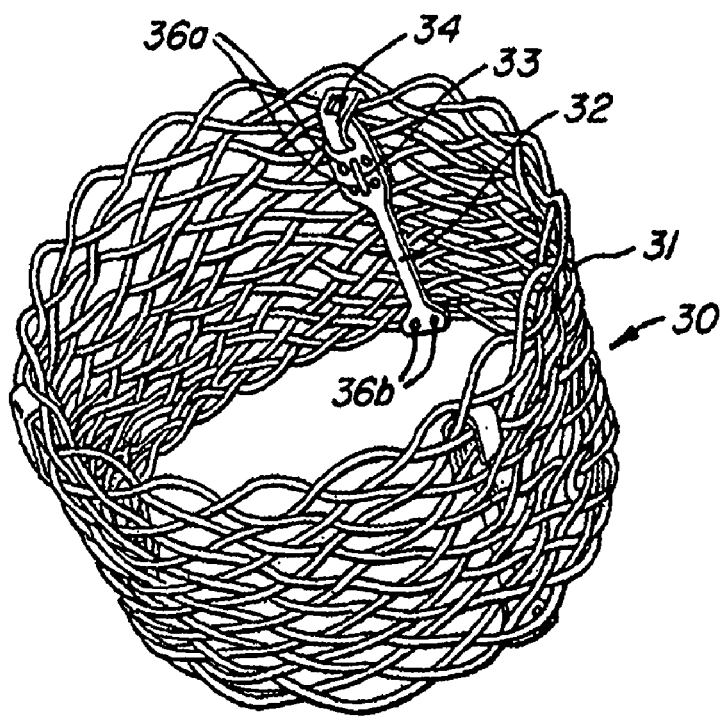
Figure 2C:
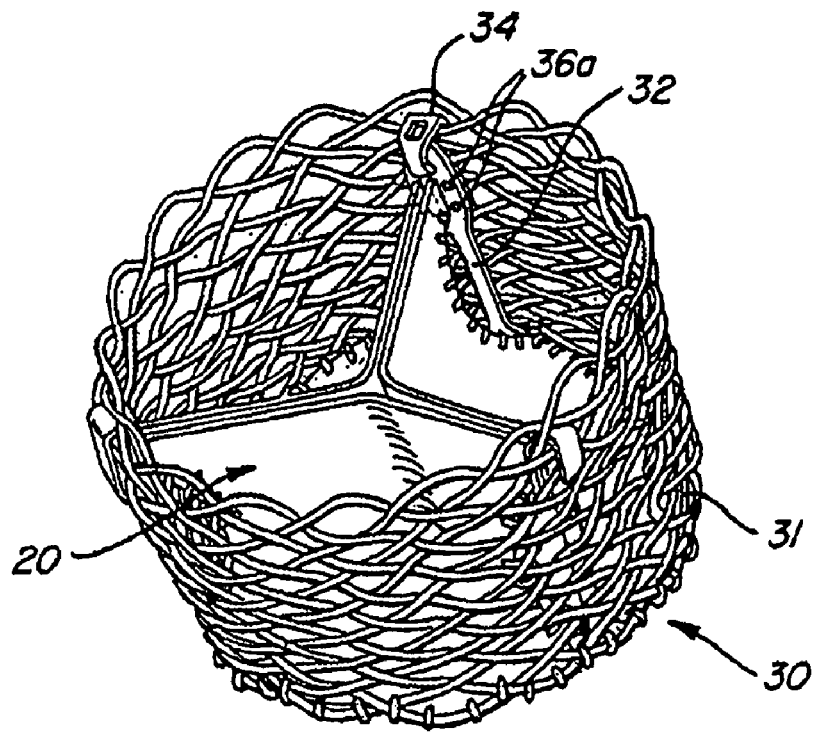

Anchor 30 has also a plurality of buckles 34 attached to its proximal region, one for each post 32. Posts 32 and buckles 34 form a two-part locking mechanism for maintaining anchor 30 in a deployed or expanded configuration (e.g., as illustrated in FIGS. 1B, 2B and 2C).

In this embodiment, anchor 30 is formed from collapsible and expandable wire braid. Anchor braid 30 is preferably self-expanding and is preferably formed from a material such as Nitinol, cobalt-chromium steel or stainless steel wire using one or more strands of wire. While the illustrated embodiment is formed from a single strand of wire, in other embodiments may benefit from a wire braid formed of 2-20 wires, more preferably 3-15 wires, or more preferably 4-10 wires.

Delivery and deployment of braided anchor 30 is similar to the delivery and deployment of the anchors described in U.S. patent publication 2005/0137688, filed Dec. 23, 2003, the disclosure of which is incorporated herein by reference. Specifically, in one embodiment described below, during deployment braided anchor 30 is actively foreshortened by proximally retracting the distal region control wires relative to control tubes 106 to expand and lock the anchor in place. In some embodiments, foreshortening expands anchor 30 to a radially symmetrical, bilaterally symmetrical, or asymmetrical expanded shape (as further described below). The foreshortening step can include expanding a first region of the anchor to a first diameter and a second region of the anchor to a second diameter larger than the first diameter. A third region may also be expanded to a diameter larger than the first diameter. The expansion of various regions of the anchor (e.g., the distal region) can be especially useful in locating the aortic valve and centering the anchor within it. Preferably, the secured anchor does not interfere with the mitral valve or the ostias. In some embodiments, the anchor is allowed to self expand prior to the foreshortening step.

As seen in FIG. 1, after endovascular delivery through sheath 110 to the vicinity of the patient's native valve (such as the aortic valve), apparatus 10 may be expanded from the collapsed delivery configuration of FIG. 1A to the expanded deployed configuration of FIG. 1B using delivery system 100. To deploy apparatus 10, external sheath 110 may be retracted relative to apparatus 10 by proximally retracting sheath handle 111 relative to control handle 120. Sheath 110 is thereby removed from the exterior of apparatus 10, permitting the anchor 30 to self-expand. In preferred embodiments, anchor 30 includes sheathing features as depicted in FIGS. 5B thru 5M or FIGS. 6, 7A, or 7D adapted to reduce sheathing force. Sheathing force is defined as the force required to push the sheath distally over the anchor or the force required to pull the anchor proximally into the sheath (as for purposes of retrieving the anchor). For example, if anchor braid 30 is composed of a shape memory material, it may self-expand to or toward its "at-rest" configuration. This "at rest" configuration of the braid can be, for example its expanded configuration, a collapsed configuration, or a partially expanded configuration between the collapsed configuration and the expanded configuration. In preferred embodiments, the anchor's at-rest configuration is between the collapsed configuration and the expanded configuration. Depending on the "at rest" diameter of the braid and the diameter of the patient's anatomy at the chosen deployment location, the anchor may or may not self-expand to come into contact with the diameter of the patient's anatomy at that location.

In its collapsed configuration, anchor 30 preferably has a collapsed delivery diameter between about 3 to 30 Fr, or more preferably 6 to 28 Fr, or more preferably 12 to 24 Fr. In some embodiments, anchor 30 in its collapsed configuration will have a length ranging from about 5 to about 170, more preferably from about 10 to about 160, more preferably from about 15 to about 150, more preferably from about 20 to about 140 mm, or more preferably from about 25 mm to about 130.

Similarly, in its expanded configuration, anchor 30 preferable has a diameter ranging between about 10 to about 36 mm, or more preferably from about 24 to about 33 mm, or more preferably from about 24 to about 30 mm. In some embodiments, anchor 30 in its expanded configuration will have a length ranging from about 1 to about 50, more preferably from about 2 to about 40, more preferably from about 5 to about 30, or more preferably from about 7 to about 20 mm.

Overall, the ratio of deployed to collapsed/sheathed lengths is preferably between about 0.05 and 0.5, more preferably about 0.1 to 0.35, or more preferably about 0.15 to 0.25. In any of the embodiments herein, anchor 30 in its expanded configuration preferably has a radial crush strength that maintains the anchor substantially undeformed in response to a pressure of up to 0.5 atm directed substantially radially inward toward the central axis, or more preferably up to 2 atm directed substantially radially inward toward the central axis. In addition, in any of the embodiments herein, the anchor has an axial spring constant of between about 10 to 250 g/cm, more preferably between about 20 to 200 g/cm, or more preferably between about 40 to 160 g/cm. In addition, in any of the embodiments herein, the anchor is preferably adapted to support the replacement valve at the anchor site in response to a differential pressure of up to 120 mm Hg, more preferably up to 240 mm Hg, or more preferably up to 320 mm Hg.

These parameters are not intended to be limiting. Additional parameters within the scope of the present invention will be apparent to those of skill in the art.

As seen in FIG. 1B, anchor 30 may be expanded to a fully deployed configuration from a partial deployed configuration (e.g., self-expanded configuration) by actively foreshortening anchor 30 during endovascular deployment. As described in more detail in U.S. patent application Ser. No. 10/746,280, the distal region of anchor 30 may be pulled proximally via a proximally directed force applied to posts 32 via a distal deployment system interface. The distal deployment system interface is adapted to expand radially during application of a proximally directed force on the distal end of the anchor. In some embodiments, foreshortening of the apparatus involves applying a proximally directed force on a deployment system interface at the distal end of the anchor. In other embodiments, foreshortening of the apparatus involves applying a distally directed force on a deployment system interface at the proximal end of the anchor. More preferably, proximally or distally directed forces on the deployment system interface do not diametrically constrain the opposite end of the anchor—distal or proximal end, respectively. When a proximally directed force is applied on the deployment system interface, it is preferably applied without passing any portion of a deployment system through a center opening of the replacement valve.

The distal deployment system interface may include control wires that are controlled, e.g., by control knob 122 of control handle 120. Similarly, the proximal regions of anchor 30 may be pushed distally via a proximal deployment system interface at the proximal end of the anchor. The proximal deployment system interface is adapted to permit deployment system to apply a distally directed force to the proximal end of anchor 30 through, e.g., fingers 106, which are controlled by, e.g., Control knob 124 of control handle 120. The proximal deployment system interface may be further adapted to expand radially during application of a distally directed force on the proximal end of the anchor. Preferably, the proximal deployment system interface is adapted to permit deployment system to apply a distally directed force on the proximal end of the anchor system through a plurality of deployment system fingers or tubes 160. Such expansion optionally may be assisted via inflation of a balloon catheter (not shown) reversibly disposed within apparatus 10, as described in U.S. patent application Ser. No. 10/746,280.

Once anchor 30 is fully deployed, posts 32 and buckles 34 of anchor 30 may be used to lock and maintain the anchor in the deployed configuration. In one embodiment, the control wires attached to posts 32 are threaded through buckles 34 so that the proximally directed force exerted on posts 32 by the control wires during deployment pulls the proximal locking end of posts 32 toward and through buckles 34. Such lock optionally may be selectively reversible to allow for repositioning and/or retrieval of apparatus 10 during or post-deployment. Apparatus 10 may be repositioned or retrieved from the patient until the two-part locking mechanism of posts 32 and buckles 34 of anchor 30 have been actuated. When the lock is selectively reversible, the apparatus may be repositioned and/or retrieved as desired, e.g., even after actuation of the two-part locking mechanism. Once again, further details of this and other anchor locking structures may be found in U.S. patent application Ser. No. 10/746,280. Locking mechanisms used herein may also include a plurality of levels of locking wherein each level of locking results in a different amount of expansion. For example, the proximal end of the post can have multiple configurations for locking within the buckle wherein each configuration results in a different amount of anchor expansion.

When apparatus 10 is placed across a patient's diseased heart valve, anchor 30 may be used to displace the patient's native valve leaflets, and replacement valve 20 will thereafter serve in place of the native valve. After final positioning and expansion, apparatus 10 may be decoupled from delivery system 100 by decoupling the proximal and distal region control wires from anchor 30. Decoupling may be actuated using knob 126 of handle 120. After decoupling, delivery system 100 then may be removed from the patient, thereby completing endovascular replacement of a patient's heart valve.

Prior to implantation of replacement valve apparatus described herein, it may be desirable to perform a valvuloplasty on the patient's diseased valve by inserting a balloon into the valve and expanding it using, e.g., saline mixed with a contrast agent. In addition to preparing the valve site for implant, fluoroscopic viewing of the valvuloplasty will help determine the appropriate size of replacement valve implant to use.

FIGS. 2A-F show further details of anchor 30 of apparatus 10. FIG. 2A shows the apparatus in a collapsed configuration, such as for delivery within a sheath or other lumen or for retrieval and recapture into a sheath or other lumen. FIGS. 2B and 2C show the anchor and valve in an expanded and locked configuration.

As shown in FIG. 2C, anchor 30 has three posts and three buckles. As seen in FIG. 2C, the three leaflets of replacement valve 20 may be coupled to the three posts 32 also known as valve supports. The posts, unlike the braid, do not collapse or expand. In some embodiments a post 32 has one or more proximal slots 33, at least one proximal hole 36*a* and at least one distal hole 36*b*. Leaflet tissue may be passed through slot 33 and sutured in place via suture routed through one or more proximal holes 36*a*. Other means known in the art for fixing valve leaflets to posts may also be employed.

Posts 32 may be coupled to anchor braid 30 via one or more distal holes 36*b*. For example, anchor braid 30 may be woven through holes 36*b*, or a suture may be routed through holes 36*b* and tied to the braid. Buckles 34 may likewise be attached to anchor braid 30 via weaving or suturing.

Figure 2D:
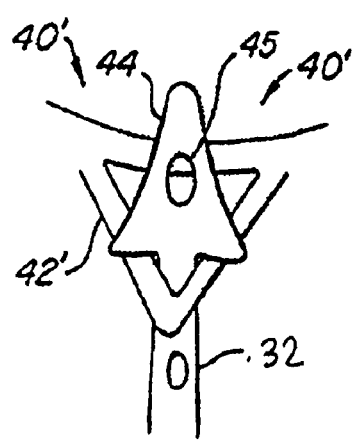

Alternative locks may be used to lock the anchor of the present invention in the foreshortened configuration. Preferably, a locking mechanism of the present invention can have multiple locking options such that locking can confer a plurality of amounts of expansion. Furthermore, the locking option can be employed asymmetrically to confer non-cylindrical shapes to the anchor. In FIG. 2D, lock 40' comprises male interlocking element 44 as described previously. However, female interlocking element 42' illustratively comprises a triangular shape, as compared to the round shape of interlocking element 42 described previously. The triangular shape of female interlocking element 42' may facilitate mating of male interlocking element 44 with the female interlocking element without necessitating deformation of the male interlocking element.

Figure 2E:
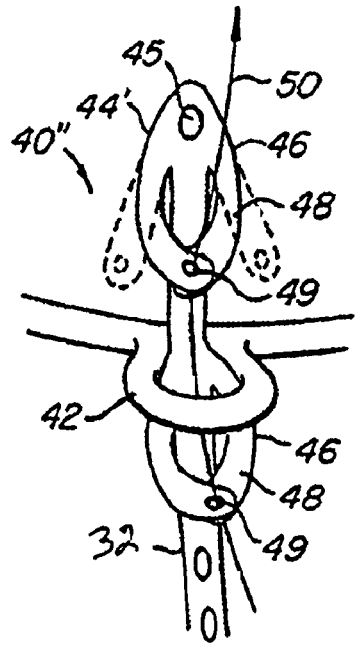
Figure 2F:
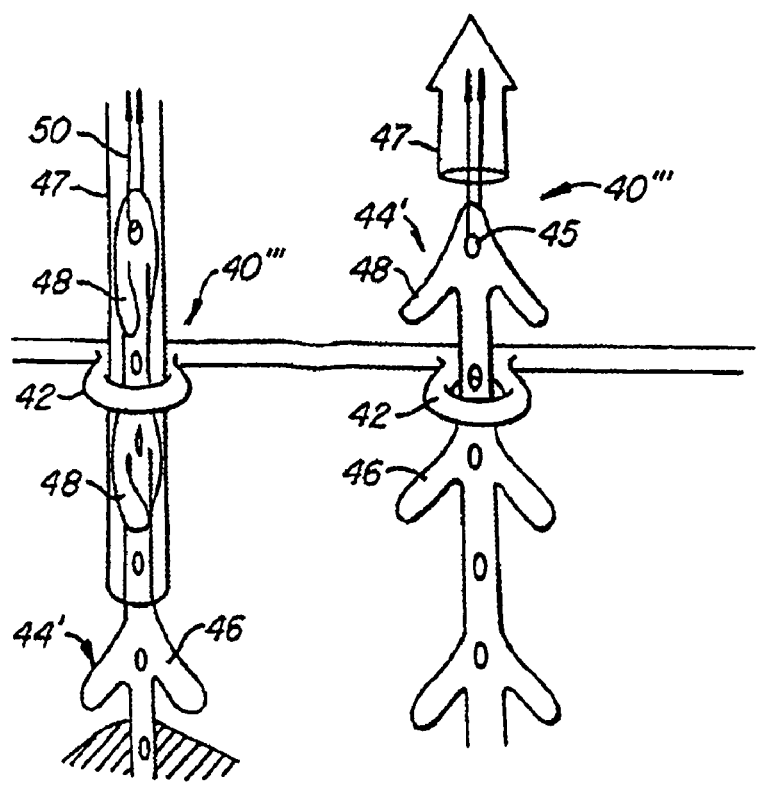

In FIG. 2E, lock 40" comprises alternative male interlocking element 44' having multiple in-line arrowheads 46 along posts 32. Each arrowhead comprises resiliently deformable appendages 48 to facilitate passage through female interlocking element 42. Appendages 48 optionally comprise eyelets 49, such that control wire 50 or a secondary wire may pass therethrough to constrain the appendages in the deformed configuration. To actuate lock 40", one or more arrowheads 46 of male interlocking element 44' are drawn through female interlocking element 42, and the wire is removed from eyelets 49, thereby causing appendages 48 to resiliently expand and actuate lock 40".

Advantageously, providing multiple arrowheads 46 along posts 32 yields a ratchet that facilitates in-vivo determination of a degree of foreshortening imposed upon apparatus of the present invention. Furthermore, optionally constraining appendages 48 of arrowheads 46 via eyelets 49 prevents actuation of lock 40" (and thus deployment of apparatus of the present invention) even after male element 44' has been advanced through female element 42. Only after a medical practitioner has removed the wire constraining appendages 48 is lock 40" fully engaged and deployment no longer reversible.

Figure 11C:

Lock 40''' of FIG. 11C is similar to lock 40" of FIG. 2E, except that optional eyelets 49 on appendages 48 have been replaced by optional overtube 47. Overtube 47 serves a similar function to eyelets 49 by constraining appendages 48 to prevent locking until a medical practitioner has determined that apparatus of the present invention has been foreshortened and positioned adequately at a treatment site. Overtube 47 is then removed, which causes the appendages to resiliently expand, thereby fully actuating lock 40'''.

Figure 3:
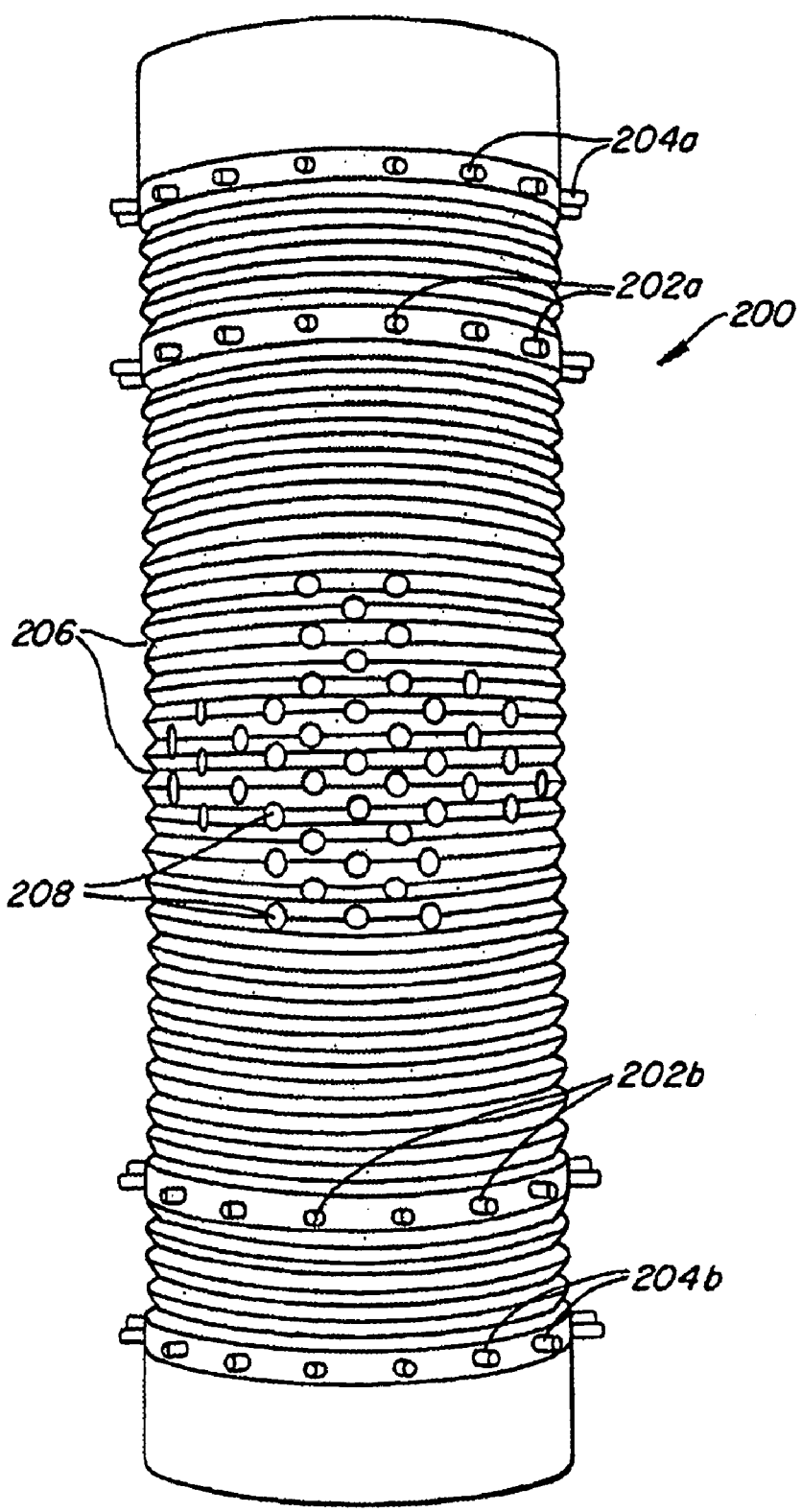
FIG. 3 is a schematic top view of an apparatus for fabricating braided anchors in accordance with the present invention.

FIG. 3 illustrates an exemplary apparatus for fabricating braided anchors. Such apparatus includes a cylindrical braiding fixture 200. The cylindrical braiding fixture 200 comprises proximal circumference of inner posts 202*a* separated by a distance x from distal circumference of inner posts 202*b*. x can be, for example, 10 to 60 mm, more preferably 20 to 50 mm, or more preferably 30 to 40 mm. Optionally, the fixture may also comprise proximal and distal circumferences of outer posts 204*a* and 204*b*, respectively. 204*a* and 204*b* can be situated about 2-10 mm from 202*a* and 202*b*, respectively. Posts 202*a/b* and 204*a/b* project from fixture 200 and may be used to route wire, e.g., for forming anchor braid 30. Inner posts 202*a* and 202*b* generally facilitate formation of a braid, while outer posts 204*a* and 204*b* generally facilitate formation of desired features at the ends of the braid, as described hereinafter with respect to FIGS. 5-8.

In some embodiments, fixture 200 comprises approximately 6-20 posts, more preferably 8-18 posts, or more preferably 10-16 posts around its circumference, though any alternative number of posts may be provided. Likewise, fixture 200 preferably has a diameter of about 2-40 mm, more preferably 4-30 mm, or more preferably 6-20 mm, though any alternative diameter may be provided. The diameter of fixture 200 preferably is the diameter of the braid in its "at rest" configuration.

Fixture 200 can optionally further comprise circumferential grooves 206 to facilitate interweaving of a first section of wire underneath an adjacent section of wire. The fixture optionally also may comprise localized depressions or holes 208 in addition, or as an alternative, to grooves 206. Depressions 208 may be provided at locations where wire segments cross to act as a visual guide for formation of anchor braid 30, as well as to facilitate the interweaving of a first section of wire beneath an adjacent section of wire.

Figure 4A:
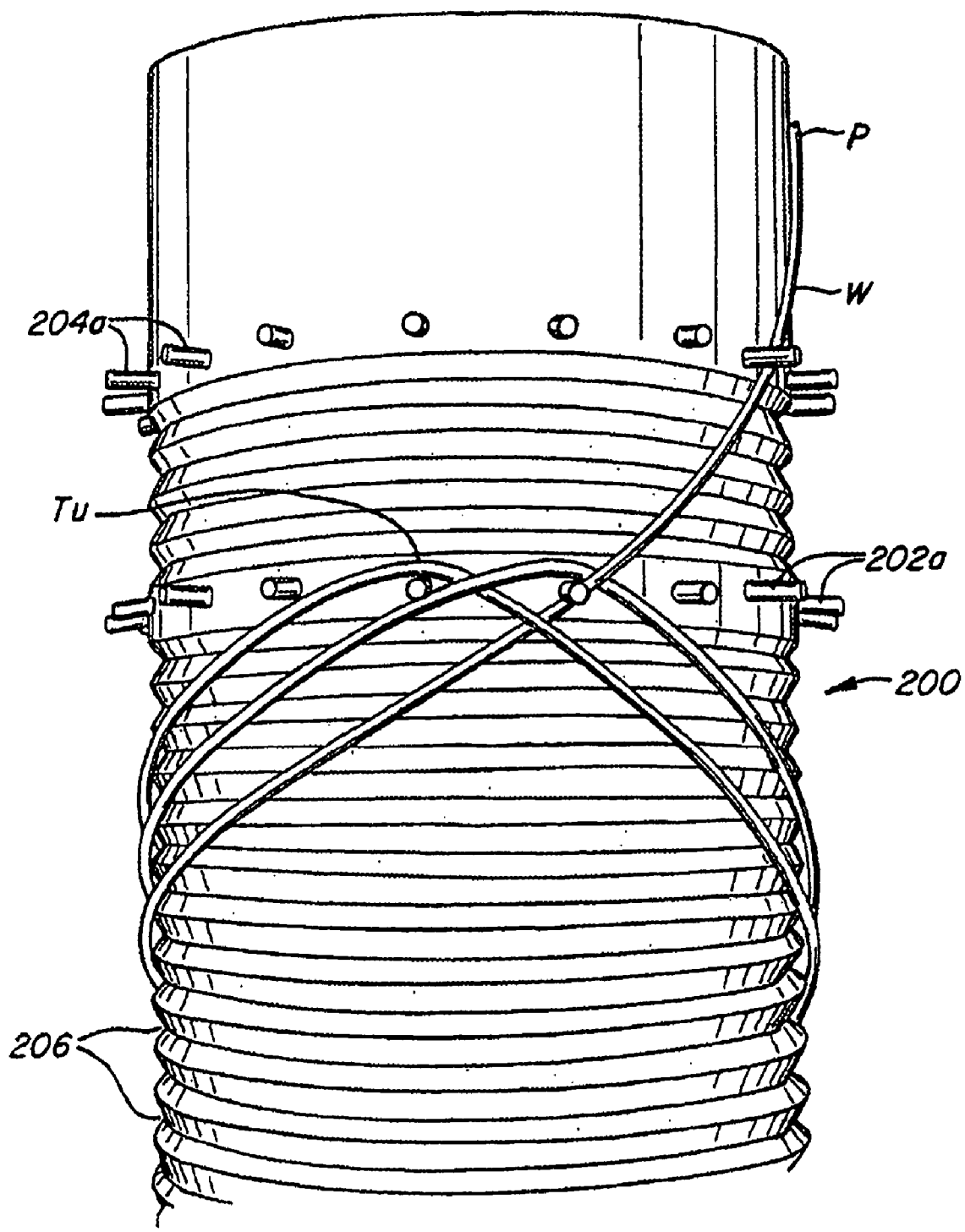
FIGS. 4A-4D are schematic top views illustrating a method of using the apparatus of FIG. 3 to fabricate a braided anchor of the present invention.
Figure 4B:
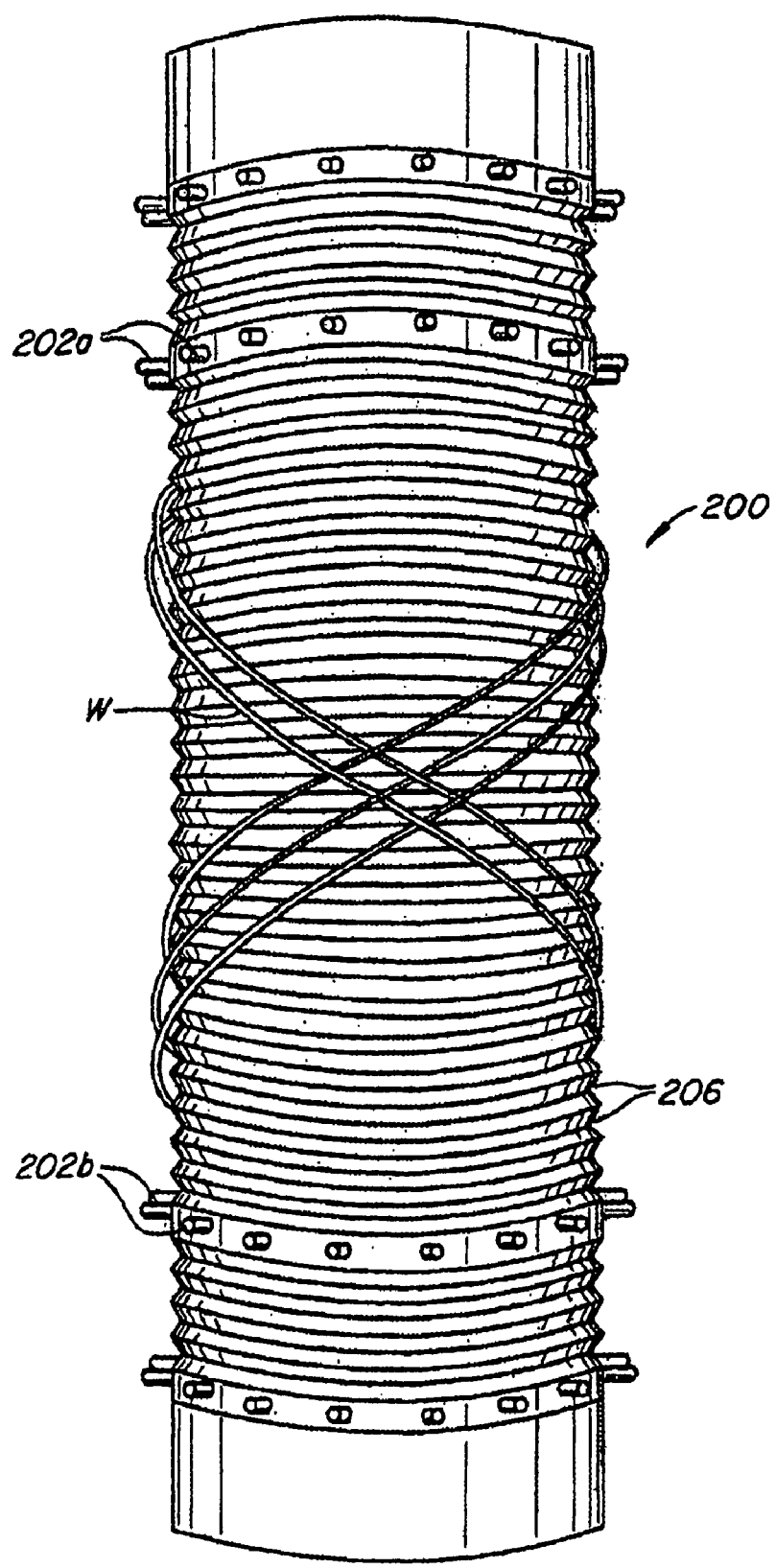
Figure 4C:
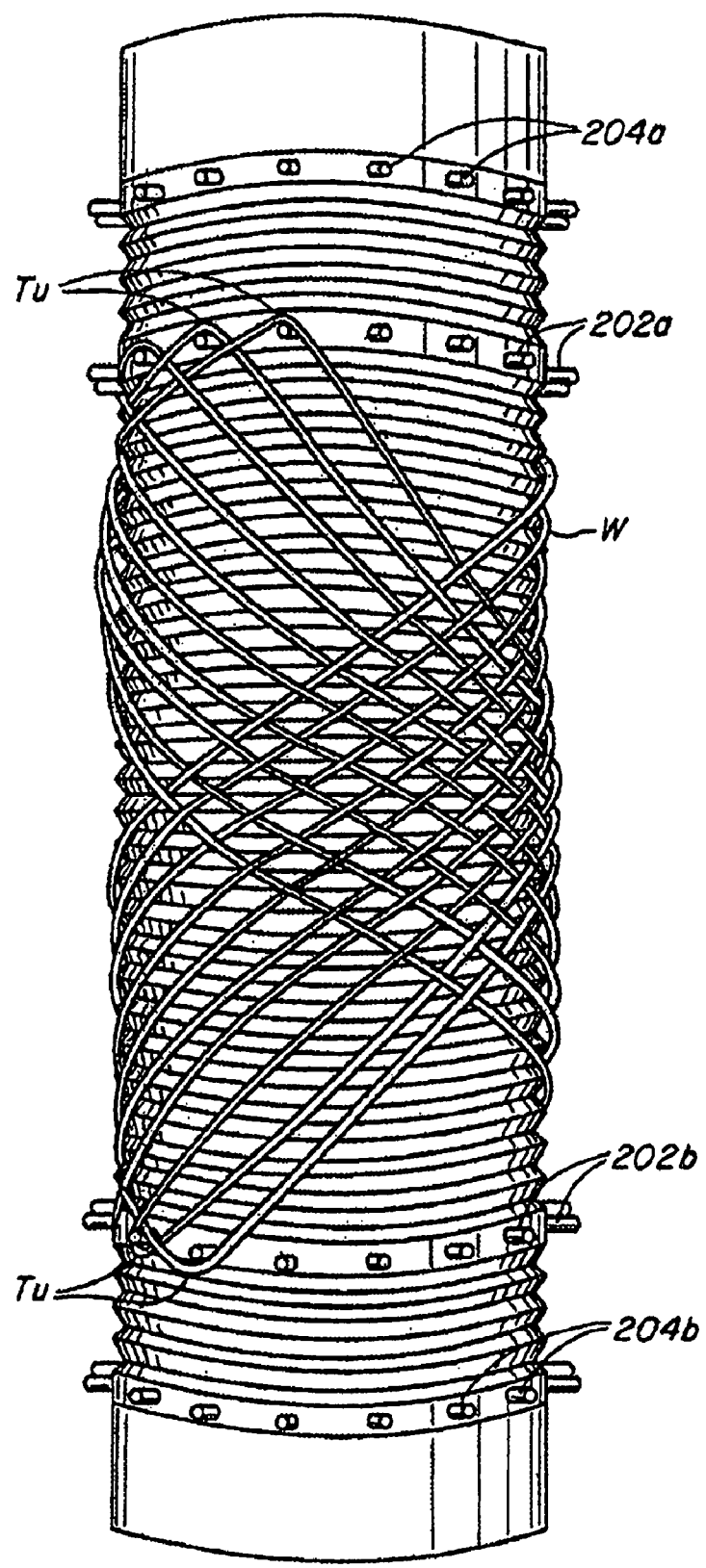
Figure 4D:
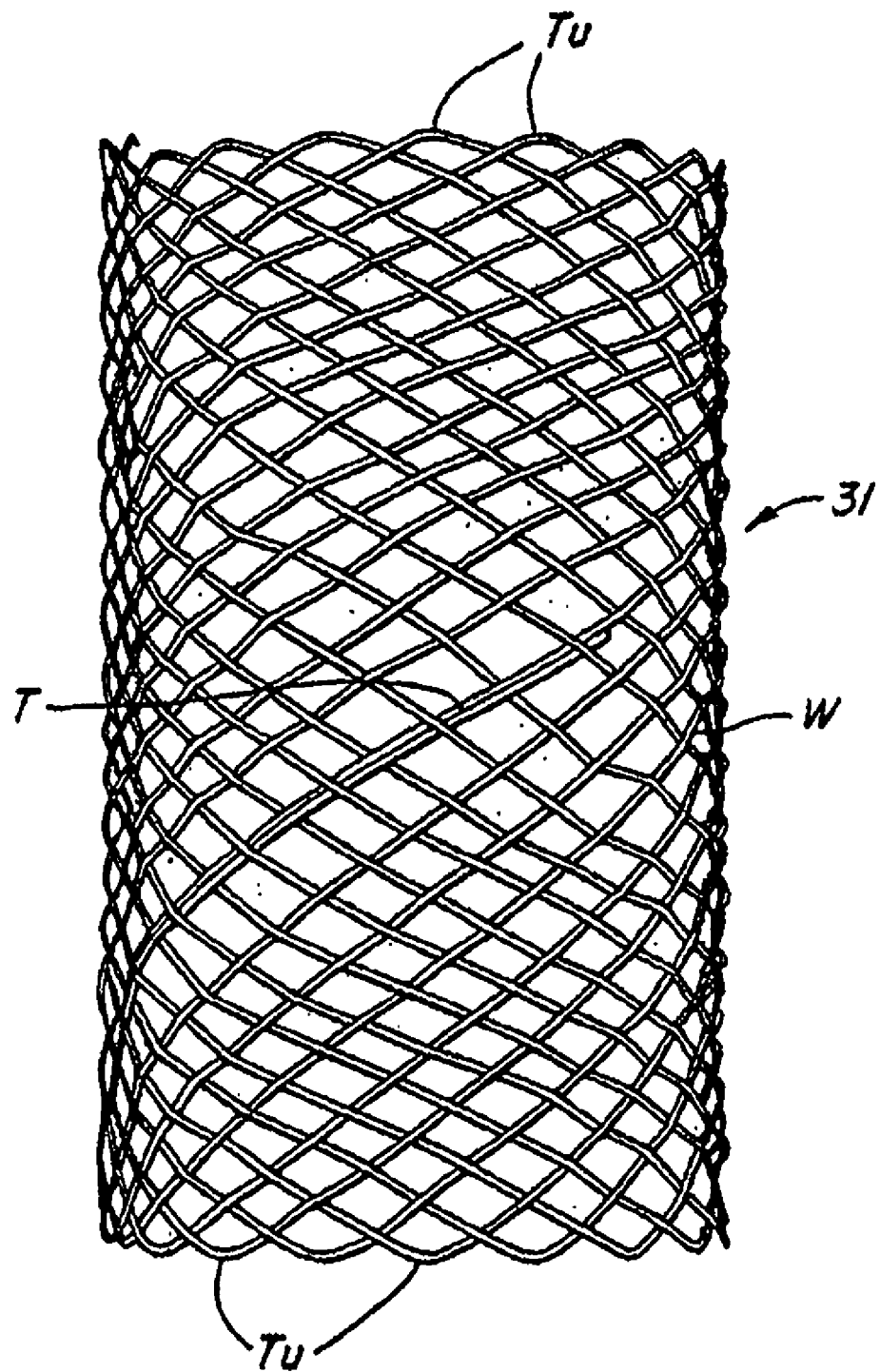

Referring now to FIGS. 4A-D, an illustrative method of using fixture 200 to fabricate braided anchors in accordance with the present invention is described. FIG. 4A provides a detail view of a proximal front side region of fixture 200 during formation of a braided anchor. FIG. 4B shows a detail backside view of a central section of the fixture. FIG. 4C shows a full-length frontside view of the fixture and FIG. 4D shows the completed braid. In FIGS. 4, anchor braid 30 is formed from a single strand of wrapped and interwoven wire W. However, it should be understood that anchor braid 30 alternatively may be formed from multiple strands of wire.

As seen in FIG. 4A, formation of anchor braid 30 begins with wire W being routed from starting position P near the proximal end of fixture 200 past outer proximal posts 204a and inner proximal posts 202a. Wire W preferably is formed from a superelastic and/or shape-memory material, such as Nitinol. However, alternative wire materials may be utilized, including Cobalt-Chromium, Steel and combinations thereof, as well as additional materials that will be apparent to those of skill in the art.

After passing inner proximal posts 202a, wire W encircles fixture 200 in a helical spiral while extending towards the distal posts, as seen in FIGS. 4B and 4C. The wire illustratively encircles fixture 200 a full 360° revolution plus one additional post. However, any alternative degree of winding may be provided (e.g., a full 360° plus 2 additional posts, a full 360° plus 3 additional posts, or a number of posts less than a full 360°). As will be apparent to those of skill in the art, altering the degree of winding will alter the expansion characteristics of the resultant braid in ways per se known.

At distal inner posts 202b, wire W forms turn Tu and is rerouted back towards proximal inner posts 202a. It should be noted that wire W can form turn Tu in either inner posts 202 or outer posts 204. Turn Tu forms a closed end of the braid. Additional sets of inner and outer posts are also contemplated. The wire once again encircles fixture 200 in a full 360° helical revolution plus one additional post before reaching the proximal inner posts and being rerouted back towards the distal inner posts. This process is repeated with the wire repetitively interwoven at crossing locations between the proximal and distal posts, e.g., via grooves 206 and/or depressions 208, to define the cells of the braid that will provide anchor 30 with desired characteristics. As seen in FIG. 4D, wire W turns both proximally and distally in order to complete formation of the braid. In this embodiment, wire W terminates in the central portion of the braid at T. Termination T may be formed, for example, by welding the wires together, applying a shrink tube about the overlap, using a crimp, braising the wires, etc. Additional techniques will be apparent to those of skill in the art.

When anchor braid 30 is formed from a shape-memory material, the braid may be heat set such that it maintains a desired degree of expansion in an at-rest configuration. The heat set at-rest configuration may comprise, for example, the delivery configuration (e.g., collapsed configuration) of FIG. 2A, the deployed configuration (e.g., expanded configuration) of FIGS. 2B and 2C, or any desired configuration therebetween. In preferred embodiments, the anchor is heat-set in a configuration between the delivery configuration and the deployed configuration. Anchor braid 30 may be heat set while still disposed on fixture 200 to maintain an at-rest configuration as formed on the fixture, which preferably is a configuration between the delivery and deployed configurations. Alternatively, the braid may be heat set after complete or partial removal from the fixture. As yet another alternative, the braid may be initially heat set while still disposed on the fixture, but thereafter may be additionally heat set in a different shape, for example, a more expanded configuration. It is expected that heat setting anchor braid 30 will provide the braid with desired delivery and/or deployment characteristics.

Figure 5N:
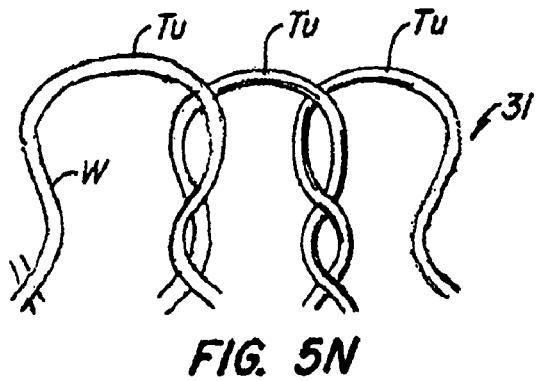
FIGS. 5A-5O are schematic detail views illustrating features of braid cells at an anchor edge.
Figure 5O:
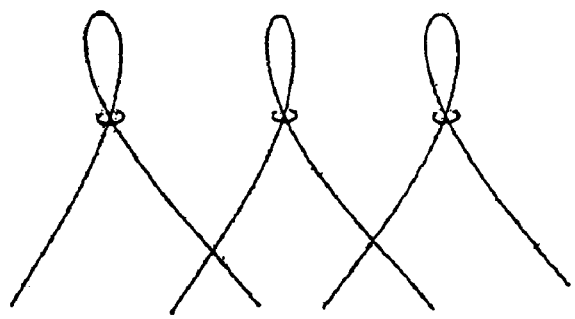

Referring now to FIGS. 5A-5O, in conjunction with FIGS. 2C and 4, an anchor braid 30 may be defined by a set of cells that is different than other cells. Such cells may be formed to provide anchor braid 30 with one or more edge features (for either or both the distal and proximal ends). These edge features can, for example, reduce or relieve stress within the braid during delivery and deployment, which in turn may reduce the incidence of anchor material fatigue caused by the pulsatile anchor motion of the anchor site. As will be apparent to those of skill in the art, forming braid 31 from a single strand of wire W (or from multiple strands of wire W that form turns or that are joined together) may lead to stress concentration at turns Tu in the wire where the wire changes direction and extends back towards the opposite end of the braid. Such stress concentration may be most pronounced while the braid is disposed in its extreme configurations, i.e. when the braid is disposed in the collapsed delivery configuration of FIG. 2A or the expanded deployed configuration of FIGS. 2B and 2C.

Stress concentration may increase the rigidity of an anchor braid and/or may impede delivery and deployment, as well as sheathing, of the braid. Thus, in preferred embodiments, a group of cells can be configured to reduce the sheathing force as described herein. Furthermore, to enhance deliverability, stress concentration may require that anchor braid 30 be fabricated from a relatively thin wire W. However, thin wire may not provide anchor braid 30 with adequate radial strength to displace a patient's diseased native heart valve leaflets and/or to anchor apparatus 10 against a patient's anatomy. Conversely, use of a relatively thick wire W may increase stiffness, thereby precluding retrograde delivery of apparatus 10, as well as a risk of kinking at turns in the braid. Thus, in some embodiments, wires varying in thickness may be used, or multiple wires having different thickness may be woven together. Also, wires made from different materials may be used to form an anchor braid.

It may be desirable to reduce stress concentration at the edges of anchor 30 where wire W changes direction and/or to reduce the circumferential stiffness of the anchor braid. The edge characteristics of the anchor may be altered by altering the shape of substantially all anchor braid cells at the anchor's edge (e.g., distal edge and/or proximal edge). Wire turns that control the shape of the edge cells may be formed within anchor braid 30 by routing wire W around optional outer posts 204 of fixture 200 during formation of the braid. FIG. 5A illustrates a detail view of a standard end turn Tu in an anchor braid resulting in a braid with substantially uniform cell size and shape. FIG. 5B illustrates a turn that has been elongated to lengthen the distance over which forces concentrated in the turn may be distributed, resulting in an anchor braid having edge cells that are longer along the anchor axis than the other cells defined by the braid. This elongated turn feature may be formed by routing the wire of braid about outer posts 204 of fixture 200, and then heat setting the wire.

FIG. 5C illustrates an alternative anchor edge cell configuration, wherein the tip of the elongated wire turn has been bent out of a cylindrical shape defined by the braid of anchor braid 30. This may be achieved, for example, via a combination of routing of wire W within fixture 200 and heat setting. The out-of-plane bend of turn Tu in the anchor edge cells in FIG. 5C may reduce stress in some configurations, and may also provide a lip for engaging the patient's native valve leaflets to facilitate proper positioning of apparatus 10 during deployment.

In FIG. 5D, a W-shaped turn feature has been formed at the wire turn, e.g., by routing the wire of anchor braid 30 about a central inner post 202 and two flanking outer posts 204 of fixture 200. As with the elongated braid cells of FIGS. 5B and 5C, the W-shape may better distribute stress about turn Tu. The anchor edge cell configuration in FIG. 5E includes a loop formed in braid 31 at the turn, which may be formed by looping wire W around an inner or outer post of fixture 200. FIG. 5F provides another alternative anchor edge cell configuration having a figure-eight shape. Such a shape may be formed, for example, by wrapping wire W about an inner post 202 and an aligned outer post 204 in a figure-eight fashion, and then heat setting the wire in the resultant shape.

In FIG. 5G, the edge cells of braid 31 include a heart-shaped configuration, which may be formed by wrapping the wire about an aligned inner and outer post of fixture 200 in the desired manner. In FIG. 5H, the edge cells of braid 31 have an asymmetric loop at turn Tu. The asymmetric loop will affect twisting of braid 31 during expansion and collapse of the braid, in addition to affecting stress concentration. In FIG. 5I, the anchor edge cells have a double-looped turn configuration, e.g. via wrapping about two adjacent inner or outer posts of fixture 200. Additional loops may also be employed. The double loop turn feature may be formed with a smooth transition between the loops, as in FIG. 5I, or may be heat set with a more discontinuous shape, as in FIG. 5J.

FIG. 5K illustrates that the edge cells of braid 31 may have multiple different configurations about the anchor's circumference. For example, the anchor edge cells shown in FIG. 5K have extended length cells as in FIG. 5B disposed adjacent to standard size edge cells, as in FIG. 5A. The anchor edge cells of FIG. 5L have an extended turn configuration having an extended loop. The anchor edge cells shown in FIG. 5M have an alternative extended configuration with a specified heat set profile. Finally, the anchor edge cells shown in FIG. 5N that overlap or are interwoven to be coupled to one another.

In preferred embodiments, the edge cells may be wrapped using wire, string, or sutures, at a location where the wire overlaps after an end turn as is illustrated in FIG. 5O. This tied-end turn feature prevents cells from interlocking with each other during deployment.

The edge cell configuration of FIG. 5 may be heat set independently of the rest of the braid. The anchor edge cell configurations of FIG. 5 are provided only for the sake of illustration and should in no way be construed as limiting. Additional turn features within the scope of the present invention will apparent to those of skill in the art in view of FIG. 5. Furthermore, combinations of any such turn features may be provided to achieve desired characteristics of anchor braid 30.

Figure 6A:
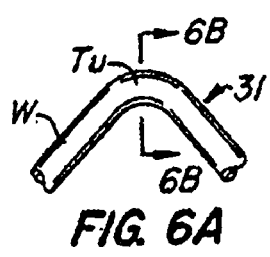
FIGS. 6A-6E illustrate further features of braid cells at an anchor edge.
Figure 6B:
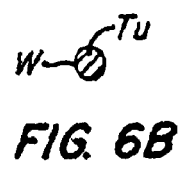
Figure 6C:
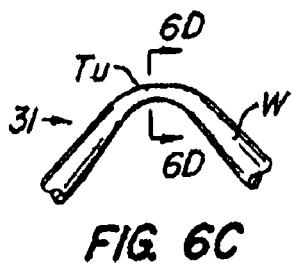

Referring now to FIGS. 6A-E, additional configurations for reducing stress concentration and/or circumferential stiffness of anchor braid 30 are illustrated. Such configurations can be used independently or in conjunction with other configurations disclosed herein. Such configurations are preferably used at the anchor's edges to locally reduce the cross-sectional area of substantially all cells or all cells in the anchor braid's edge (e.g., proximal and/or distal). As seen in FIGS. 6A and 6B, turns Tu in wire W typically may have a substantially continuous (e.g., round) cross-sectional profile. As seen in FIG. 6C, modifying the edge cell configuration by locally reducing the thickness or cross-sectional area of wire W at turn(s) Tu will reduce stress concentration within the wire at the turns and facilitate collapse and/or expansion of anchor braid 30 from the delivery to the deployed configurations. Furthermore, it is expected that such localized reduction in thickness or cross-sectional area will reduce a risk of kinking, fatigue or other failure at turns Tu.

Figures 6D, 6E:
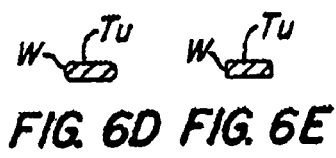

Localized reduction may be achieved via a localized etching and/or electropolishing process. Alternatively or additionally, localized grinding of the turns may be utilized. Additional processing techniques will be apparent to those of skill in the art. As seen in FIGS. 6D-6E, wire W may, for example, comprise an oval or rectangular cross-sectional profile, respectively, after localized reduction. The wire alternatively may comprise a round profile of reduced cross-sectional area (not shown). Additional profiles will be apparent. Localized reduction can take place at any time (e.g., before or after a braid is woven). Preferably, localized reduction occurs after weaving. However, in some embodiments, a wire of a given length may be etched or ground at preset segments and subsequently woven.

Figure 7A:
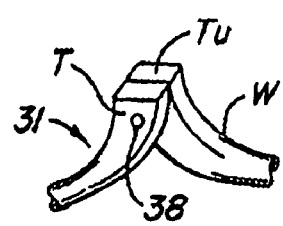
FIGS. 7A-7J are schematic detail views terminations for one or more wire strands forming anchors of the present invention.
Figure 7B:
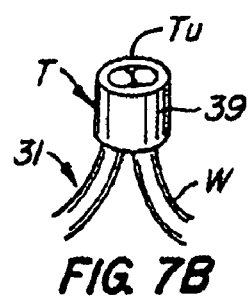
Figure 7C:
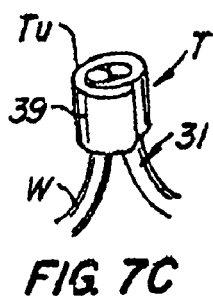

Referring now to FIGS. 7A-J, instead of terminating the beginning and end of wire W of braid 31 at an overlap within the braid, as discussed previously, the two ends of the wire may be terminated at the anchor's edge. Likewise, when braid 31 is fabricated from multiple wires W, the wires (or a subset of the wires) optionally may be joined together or terminated at turn(s) of the braid. In FIG. 7A, wire termination T at the ends of wire(s) W comprises a hinged termination with hinge post 38. In FIG. 7B termination T comprises a clipped or crimped termination with end cap 39. In FIG. 7C, cap 39 is wrapped about the ends of wire W to form wrapped termination T.

Figure 7D:
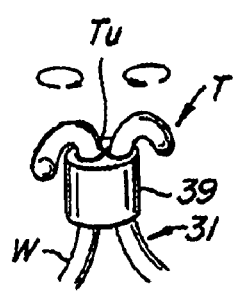
Figure 7E:
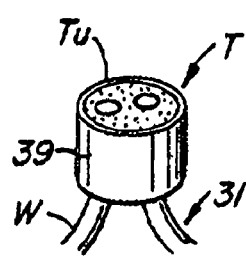
Figure 7F:
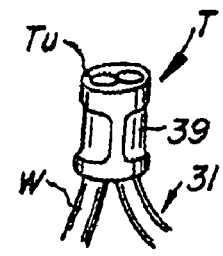
Figure 7G:
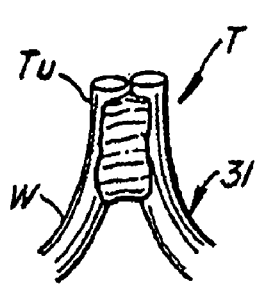
Figure 7H:
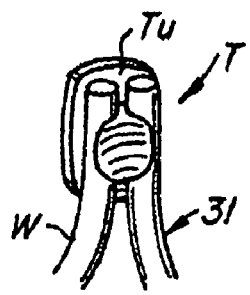
Figure 7I:
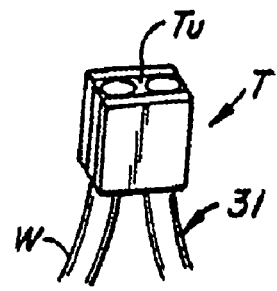
Figure 7J:
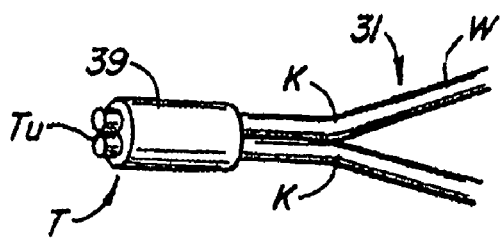

In FIG. 7D, cap 39 is placed over the wire ends, which are then bent to provide a swivel termination. In FIG. 7E, the wire ends are potted within cap 39 at termination T. In FIG. 7F, cap 39 is swaged about the wire ends. In FIG. 7G, the wire ends are welded or glued together. In FIG. 7G, the wire ends are spot welded together. Alternatively, the wire ends may be braised to form termination T, as in FIG. 7H. As yet another alternative, cap 39 may be placed about the wire ends, and kinks K may be formed in wire W to provide the ends of the wire with an 'over-center' bias that maintains termination T, e.g., swivel termination T. Additional terminations will be apparent to those of skill in the art.

Figure 8A:
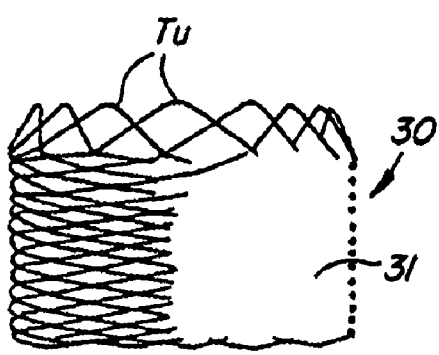
FIGS. 8A and 8B are schematic side views of alternative embodiments of the anchor portion of the apparatus of the present invention.
Figure 8B:
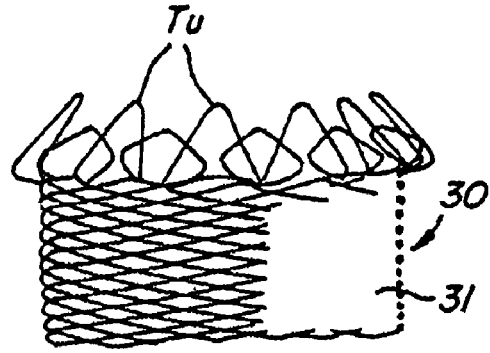

With reference now to FIGS. 8A-B, alternative anchors of the present invention are described having anchor edge features that facilitate sheathing of the apparatus and reduce the sheathing force. In FIG. 8A, the edge cells of anchor 30 have inwardly canted configurations at the wire turns Tu about a proximal circumference of the anchor. These edge cell configurations provide the proximal circumference with a conical profile that facilitates sheathing of the apparatus within a delivery system, e.g., previously described delivery system 100, by allowing collapse of anchor 30 to proceed in a more gradual and/or continuous manner, and funneling the anchor into the sheath.

FIG. 8B illustrates another alternative anchor 30 having edge cell configurations formed by wire turns Tu about its proximal circumference that first cant outward, and then cant inward. The inward cant provides the proximal circumference with a conical profile and may facilitate sheathing, while the outward cant may facilitate anchoring at a treatment site, e.g., may engage a patient's native valve leaflets. As will be apparent, the edge cell configurations of FIG. 8, as well as those of FIGS. 5-7, optionally may be provided at either the proximal or distal ends of the anchor, or both. The edge cell configurations of FIG. 8, as well as those of FIGS. 5 and 7, may, for example, be formed by heat setting braid 31 in the desired configuration.

Referring now to FIG. 9, further alternative anchors are described having edge cell configurations adapted to lock the anchor in the deployed configuration to maintain expansion. In FIG. 9A, anchor 30 comprises elongated, hooked edge cells formed from wire turns Tu that are configured to snag braid 31 and maintain the anchor in the deployed configuration, as shown. In FIG. 9B, the hooked turn features have been elongated, such that the hooks are configured to snag the opposing end of anchor 30 to maintain expansion.

Figure 9A:
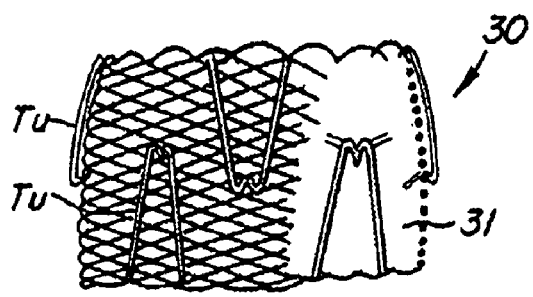
FIGS. 9A-9E are schematic side views of further alternative embodiments of the of the anchor portion of the apparatus of the present invention.
Figure 9B:
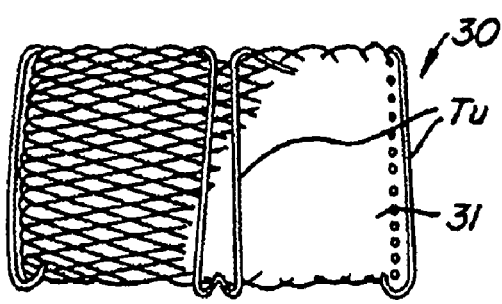
Figure 9C:
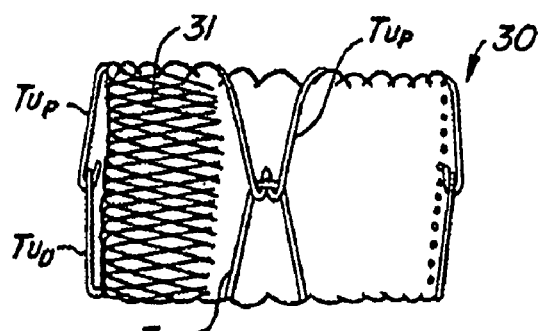
Figure 9D:
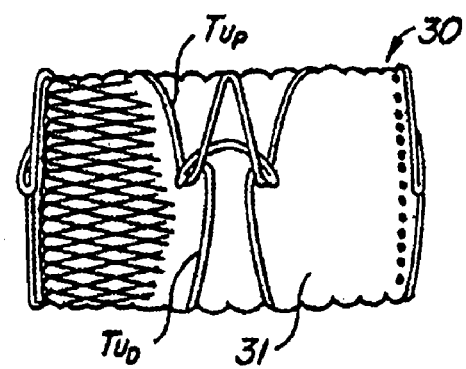
Figure 9E:
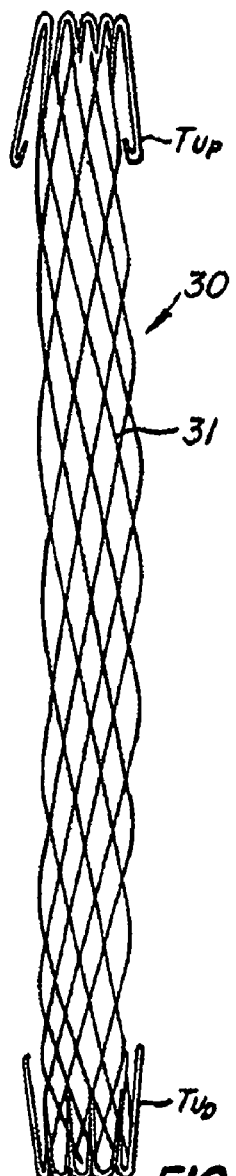

In FIG. 9C, anchor edge cells defined by wire turns TuP and distal turn features TuD are configured to interlock between the ends of anchor braid 30 in order to maintain the deployed configuration of anchor 30. The proximal edge cells form a hook adapted to engage elongated turns of the distal turn features. As will be apparent, the disposition of all or a portion of the proximal and distal edge cell configurations optionally may be reversed, i.e. the proximal edge cells may form hooks and the distal edge cells may be configured as elongated turns. FIG. 9D illustrates interlocking proximal and distal edge cell configurations of more complex geometry. FIG. 9E illustrates interlocking proximal and distal edge cell configurations while anchor 30 is disposed in the collapsed delivery configuration. The locking turn features of FIGS. 9 may, for example, be formed by heat setting anchor braid 30 (or locking features only) in the desired configuration. Additional locking turn features will be apparent to those of skill in the art. In preferred embodiments, the anchor locking mechanism can be set to have alternative locking options that allow for various amounts of expansion.

Figure 10A:
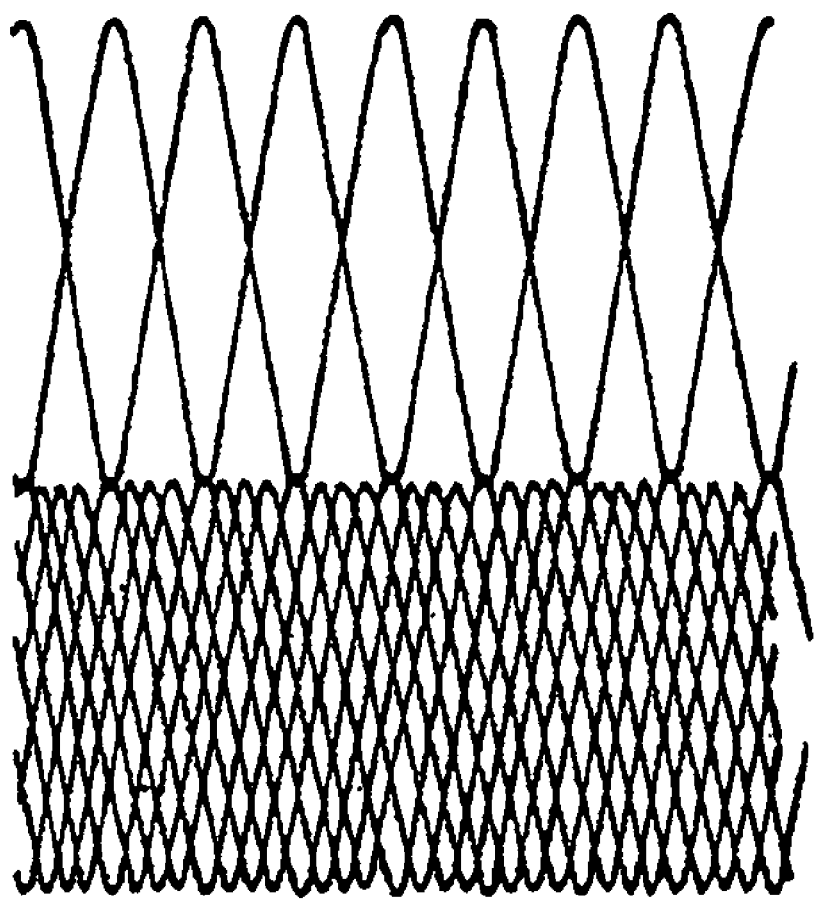
FIGS. 10A-10D are schematic views of different weave configurations.
Figure 10B:
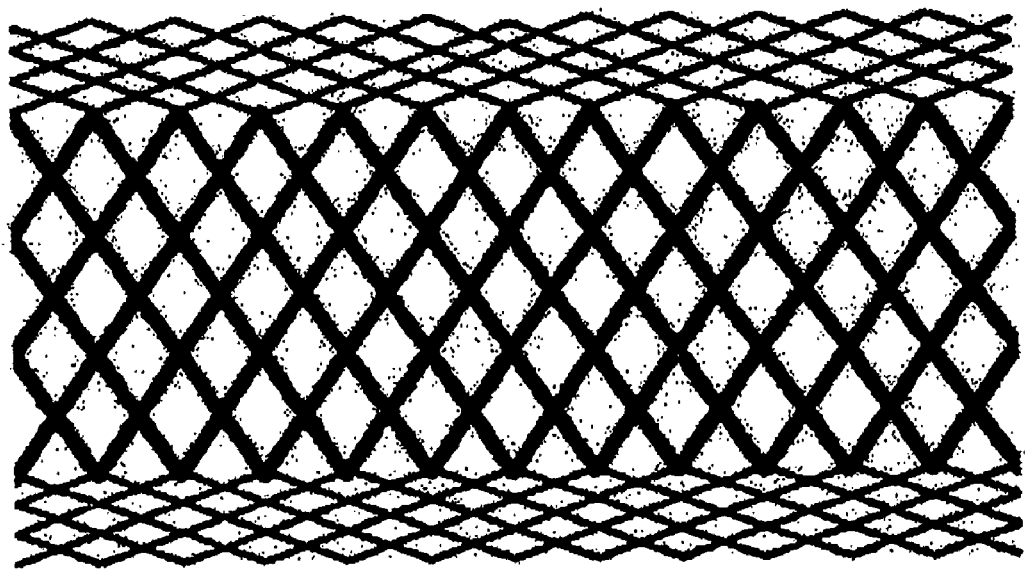
Figure 10C:
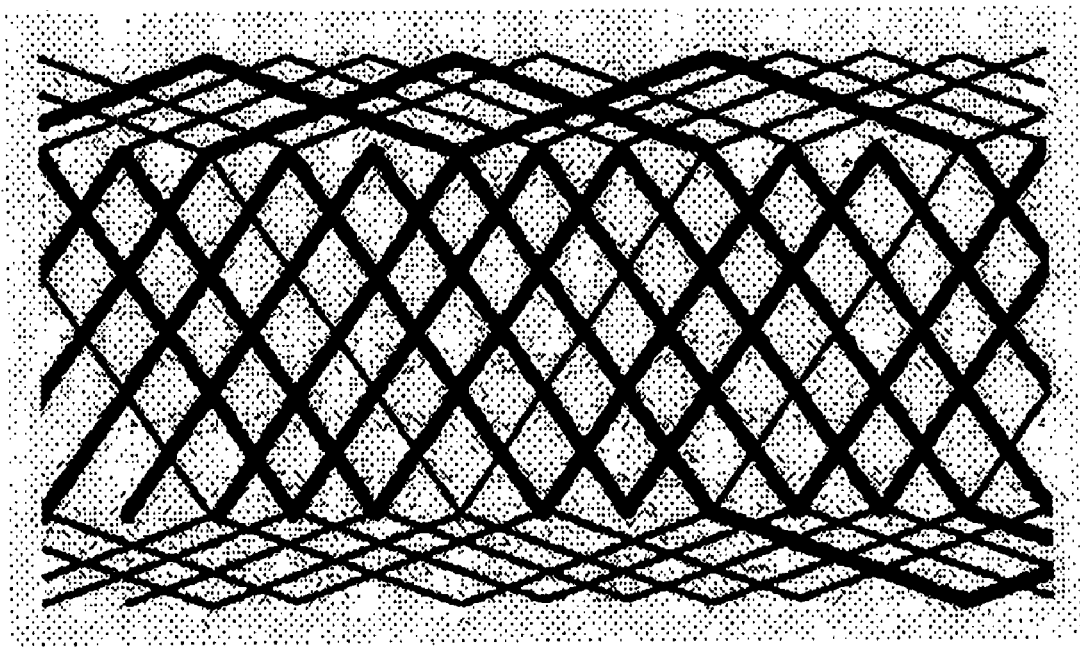
Figure 10D:
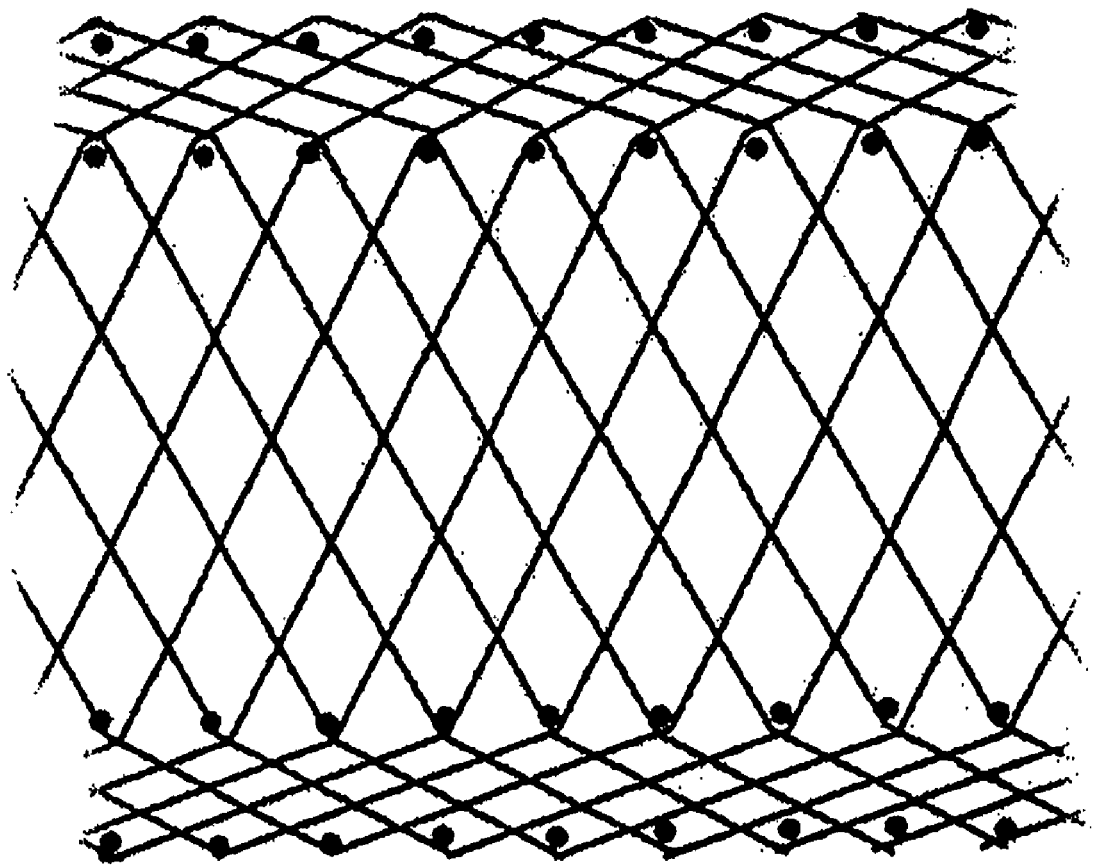

FIGS. 10A-10D illustrate various embodiments of anchor braids. An anchor braid can be made of one or more wire and can be used to form various density braids. The density of the braid can be assessed by the size of cells formed by the weave. In some embodiments, two or more different density braids may be woven together. For example, FIG. 10A illustrates two groups of cells or two braids interwoven in the center. The top group of cells forms a more open weave than the bottom group of cells, which forms a denser weave. FIG. 10B illustrates another embodiment of an anchor braid having three groups of cells. The top and bottom (proximal and distal) edges of the anchor braid have denser cells than the central portion of the anchor. Also, the edges of the anchor are woven from a thinner filament than the central portion. In another embodiment illustrated by FIG. 10C, all three sections of an anchor valve are woven by more than one wire. The wires of each section are made of a different material and/or thickness. Wires at the sectional boundaries may or may not interconnect with wires from a different section. Each of the sections of the braid anchor may be composed of a different number of wires. FIG. 10D illustrates another embodiment of a braided anchor having three sections. In this embodiment, all sections are composed of a single wire. The proximal and distal sections/edges of the braided anchor have the same pitch. The central region of the braided anchor has a different pitch than the edge sections.

FIGS. 11A-11E illustrate side views of braided anchor having more than one braid pitch. Varying pitch within the anchor allows localized variations in foreshortening across the anchor, as greater foreshortening is achieved by higher pitch of the braid. Moreover, the localized foreshortening features allow for the design of a braid which incorporates various diameters depending upon the amount of foreshortening. (The greater the foreshortening, the greater the diameter increase upon deployment.)

Figure 11D:
Figure 11E:

FIG. 11A, for example, is a side view representation of braided anchor of FIG. 10D. On the left side of the figure, the expanded anchor is illustrated having a denser weave (shorter pitch) at the distal and proximal ends; hence the dots are located closer to each other. The middle section of the anchor is composed of a looser weave that is generated by a higher pitch braid and is represented by dots that are farther away from each other. On the right side of the figure, the braided anchor is foreshortened and the dots are collapsed closer to each other. In this case, the central portion of the anchor foreshortened more than the proximal and distal edges. FIG. 11B illustrates a side view of a foreshortened braided anchor that is created by low pitch at the edges and high pitch in the middle. FIG. 11C illustrates a side view of a foreshortened braided anchor that is created by high pitch edges and low pitch middle section. FIG. 11D illustrates a side view of a foreshortened braided anchor that includes a sealing feature or space filling feature at both ends. This type of anchor can be created by a high pitch braid at edges, low pitch braid in the middle and heat setting the edges to curl upon unsheathing. This end feature is useful in facilitating anchoring by functioning as a locator and sealing. FIG. 11E illustrates a side view of a foreshortened braided anchor that is associated with an everting valve or locational features.

In preferred embodiments, the middle section of the anchor may be composed of thicker wire(s) than edge section(s)

Figure 12A:
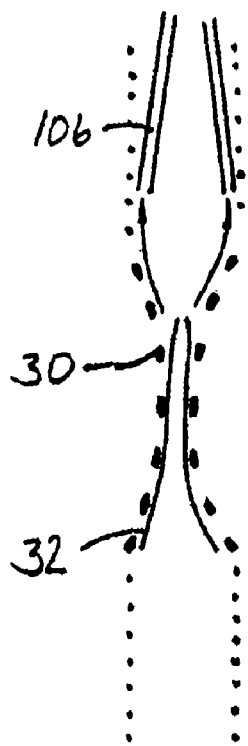
FIGS. 12A-12E are schematic side views of a deployment process.
Figure 12B:
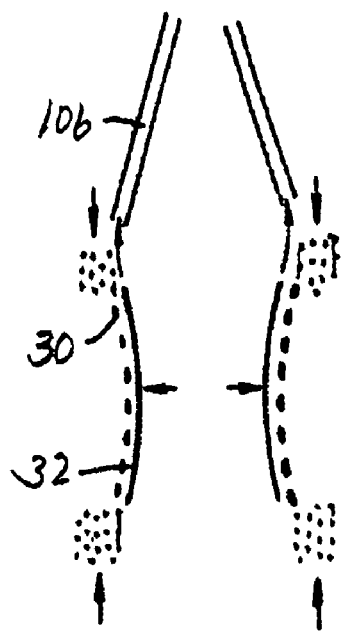
Figure 12C:
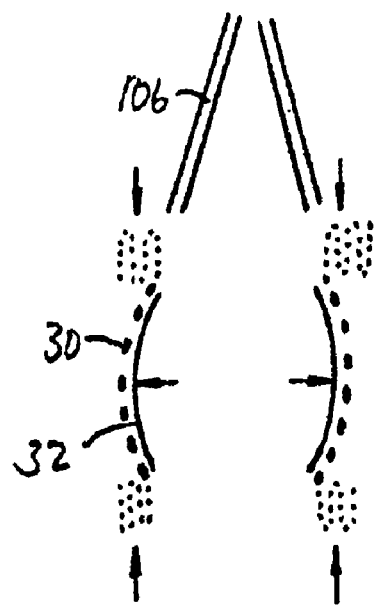
Figure 12D:
Figure 12E:
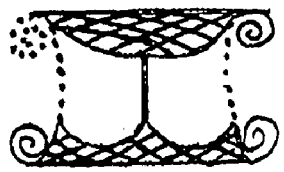

FIGS. 12A-12C illustrate an example of the process of deploying the anchor, such as the one illustrated in FIG. 11B above. FIG. 12A illustrates a braided anchor 30 in its expanded configuration. The anchor is composed of three sections. The distal and proximal sections of the anchor are made of a fine weave (low pitch) braid. The middle section of the anchor is made of a higher pitch braid and are preferably heat set to roll upon unsheathing. Furthermore, in preferred embodiments, the filaments of the distal and proximal sections may be thinner (e.g. .005 in thickness) than the filaments of the middle section (e.g., .010 in thickness). Posts 32 are coupled to the middle section of the anchor. For deployment, tubes 106 are coupled to the anchor's middle section. FIG. 12B illustrates the process of deployment. As the anchor is pushed distally by the tubes and pulled proximally by wires, it is unsheathed and begins foreshortening. The distal section rolls up and can act as a locator, assisting the operator in locating the aortic valve. It then functions as a seal preventing leakage. The proximal section may optionally also roll up. In FIG. 12C, the device may be configured such that the middle section of the valve may form an hour glass shape or a round shape. The tubes may subsequently be removed as described before. FIG. 12D is another illustration of the braided anchor in its elongated configuration. FIG. 12E is another illustration of the braided anchor in its foreshortened configuration.

Figure 13A:
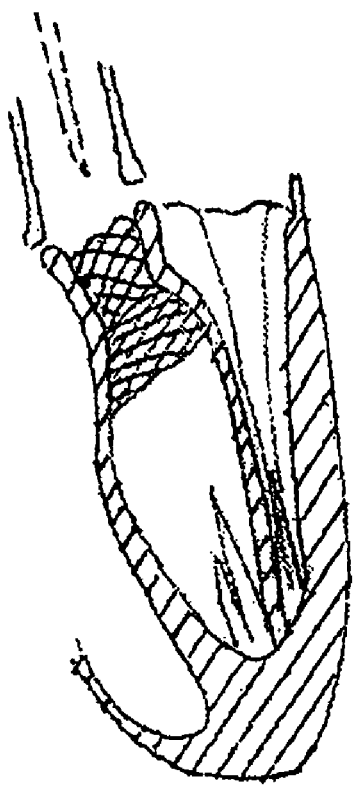
FIGS. 13A and 13B illustrate a braided anchor in the heart.
Figure 13B:
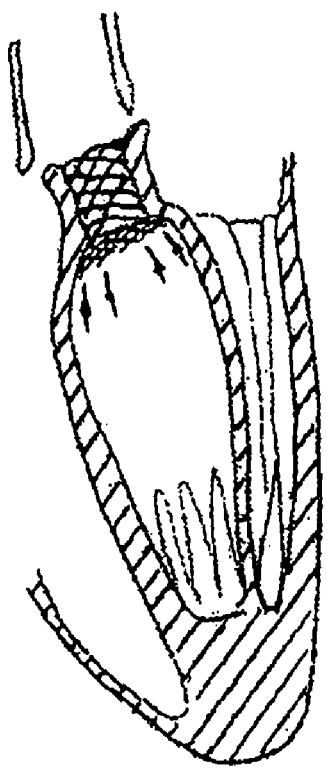

FIGS. 13A-13B illustrate another embodiment of a braided anchor. In this embodiment, the anchor includes two sections—a distal section made of a fine weave and a higher pitch braid than the proximal section. In FIG. 13A the device is deployed such that the distal section made of the fine weave is distal to the aortic valve. In FIG. 13B, the distal section is foreshortened, either by heat set memory or actively. The foreshortening of the distal section allows the operator to locate the valve and situate the anchor prior to release.

Figure 14A:
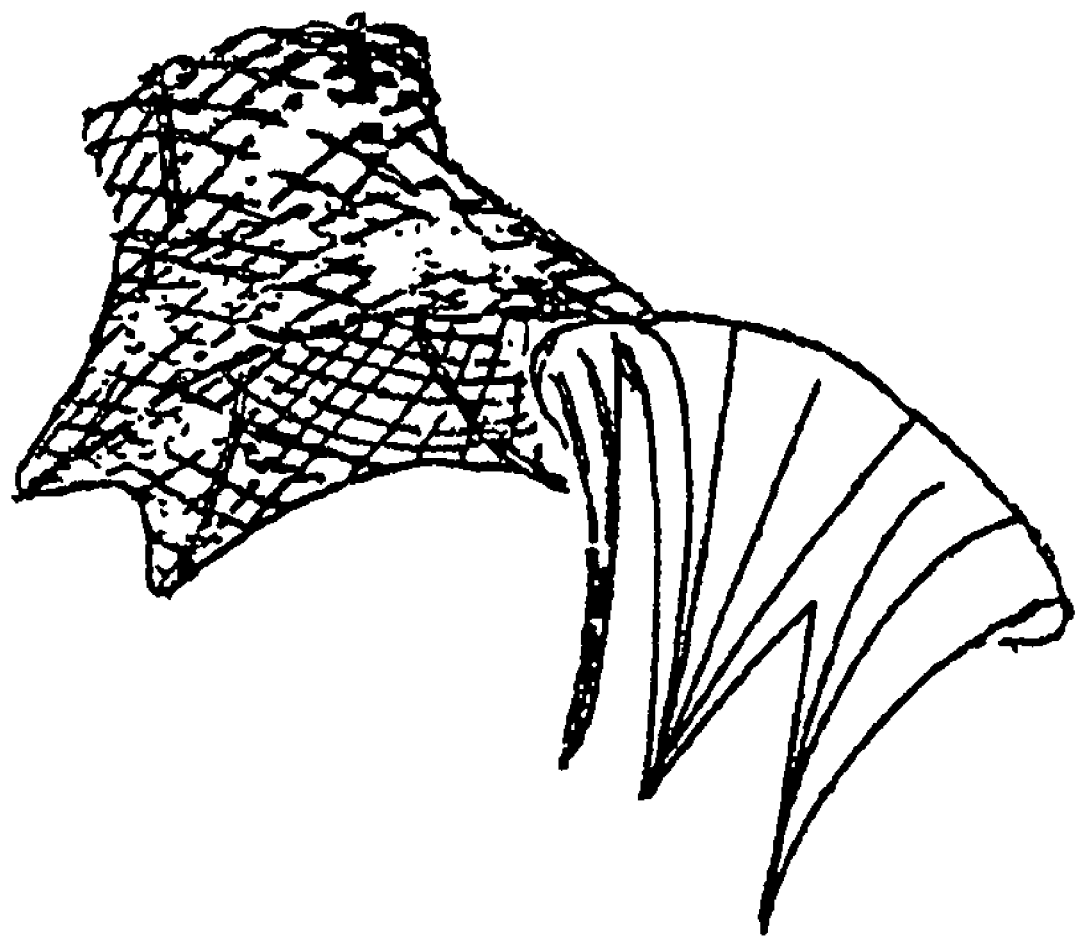
FIGS. 14A and 14B illustrate a bilaterally symmetrical anchor and an asymmetric anchor, respectively.
Figure 14B:
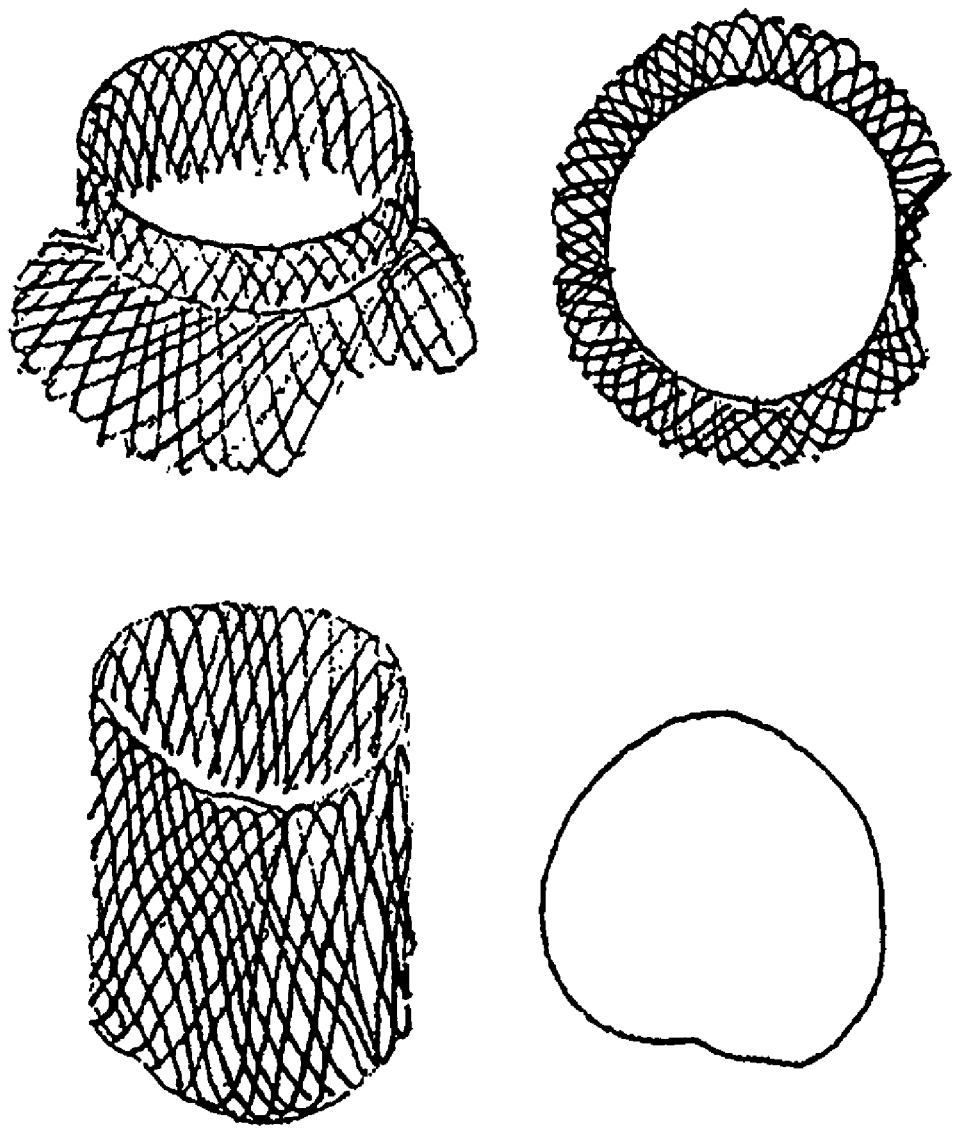

The anchors described herein can be, for example, radially symmetrical, bilaterally symmetrical, or asymmetrical. A radially symmetrical anchor is one for which symmetry exists across any diameter. A bilaterally symmetrical anchor is one for which symmetry exists across a finite number if diameters). An asymmetrical anchor is one for which there exists no diameter across which a symmetry may be found. FIG. 2B illustrates one embodiment of a radially symmetrical anchor. FIG. 14A illustrates one embodiment of a bilaterally symmetrical anchor. FIG. 14B illustrates two embodiments (side and top views) of asymmetrical anchors. The benefits of bilaterally symmetrical an asymmetrical anchors is their ability to avoid interfering with anatomical features, such as, for example the coronary ostial and/or mitral valve. Thus, in preferred embodiments, a braided anchor includes a region adapted to prevent expansion of the anchor into the mitral valve, as is illustrated in FIG. 14A.

While preferred embodiments of the present invention are shown and described herein, it will be obvious to those skilled in the art that such embodiments are provided by way of example only. Numerous variations, changes, and substitutions will occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for replacing a heart valve, comprising:
an expandable, braided anchor and a replacement heart valve secured to the expandable, braided anchor, and a deployment system;
wherein the expandable, braided anchor has a delivery configuration within a delivery device, a partially-deployed self-expanded configuration, and a fully deployed configuration,
wherein the expandable, braided anchor comprises a distal lock element disposed on a distal region of the expandable, braided anchor and a proximal lock element disposed on a proximal region of the expandable, braided anchor,
wherein the deployment system is reversibly coupled to the expandable, braided anchor; and
wherein the distal lock element and the proximal lock element are adapted to engage one another in the fully deployed configuration to lock the expandable, braided anchor in the fully deployed configuration, the distal lock element and the proximal lock element disengaged from one another when the expandable, braided anchor is in the delivery configuration.

2. The apparatus of claim 1, wherein the braid has at least one closed end.

3. The apparatus of claim 1, wherein the braid is heat-set in the partially deployed self-expanded configuration such that the expandable anchor is adapted to self-expand from the delivery configuration to the partially-deployed self-expanded configuration.

4. The apparatus of claim 1, wherein the deployment system is reversibly coupled to the distal lock element.

5. The apparatus of claim 4 wherein the deployment system is adapted to apply a proximally directed force on the distal lock element to foreshorten the expandable anchor from the partially-deployed self-expanded configuration to the fully deployed configuration.

6. The apparatus of claim 1, wherein the deployment system is reversibly coupled to a proximal end of the expandable anchor.

7. The apparatus of claim 6 wherein the deployment system is adapted to apply a distally directed force to the proximal end of the expandable anchor to foreshorten the expandable anchor from the partially-deployed self-expanded configuration to the fully deployed configuration.

8. The apparatus of claim 7 wherein the deployment system comprises a plurality of actuation elements which are adapted to radially expand when the expandable anchor self-expands from the delivery configuration to the partially-deployed self expanded configuration outside of the delivery device.

9. The apparatus of claim 1 wherein the replacement heart valve is coupled to the distal lock element.

10. An apparatus for replacing a heart valve, comprising:
an expandable anchor having an unexpanded configuration and an expanded configuration, a proximal region and a distal region, the expandable anchor secured to a replacement heart valve, wherein the expandable anchor and the replacement heart valve are adapted to be endovascularly delivered within a delivery device to the vicinity of a heart valve,
wherein the expandable anchor comprises:
a braided shape memory material,
a first edge,
at least one buckle disposed at the proximal region of the expandable anchor, and
at least one interlocking element, the at least one interlocking element being disengaged from the buckle in the unexpanded configuration and engaged to the at least one buckle in the expanded configuration,
the braided shape memory material having closed ends, the closed ends defined by turns at the first edge,
wherein the braided material defines a plurality of cells, at least a first set of cells at the closed ends of the braid having a different configuration than a second set of cells in the braid.

11. The apparatus of claim 10 wherein the first set of cells are larger than the second set of cells in the braid.

12. The apparatus of claim 10 wherein the first set of cells are smaller than the second set of cells in the braid.

* * * * *